United States Patent
Nieten et al.

(10) Patent No.: US 10,145,738 B2
(45) Date of Patent: Dec. 4, 2018

(54) OPTICAL FILTER SYSTEM AND FLUORESCENCE DETECTION SYSTEM

(71) Applicant: Carl Zeiss Meditec AG, Jena (DE)

(72) Inventors: Christoph Nieten, Jena (DE); Enrico Geißler, Jena (DE); Kai Wicker, Jena (DE); Alois Regensburger, Erlangen (DE); Helge Jess, Oberkochen (DE); Roland Guckler, Ulm (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/905,052

(22) Filed: Feb. 26, 2018

(65) Prior Publication Data

US 2018/0180477 A1  Jun. 28, 2018

Related U.S. Application Data

(63) Continuation of application No. PCT/EP2016/001484, filed on Sep. 1, 2016.

(30) Foreign Application Priority Data

Sep. 1, 2015 (DE) .................... 10 2015 011 429

(51) Int. Cl.
*G01N 21/64* (2006.01)
*G01J 3/02* (2006.01)
(Continued)

(52) U.S. Cl.
CPC .......... *G01J 3/0229* (2013.01); *G01J 3/4406* (2013.01); *G01N 21/6458* (2013.01);
(Continued)

(58) Field of Classification Search
CPC ....... G01N 21/6458; G01N 2021/6419; G01N 2021/6421; G02B 26/007; G02B 21/16
See application file for complete search history.

(56) References Cited

U.S. PATENT DOCUMENTS

| 4,750,837 A * | 6/1988 | Gifford | ................ G01N 21/255 |
| | | | 250/458.1 |
| 4,802,768 A * | 2/1989 | Gifford | ................ G01N 21/255 |
| | | | 250/458.1 |

(Continued)

FOREIGN PATENT DOCUMENTS

DE  10 2010 033 825 A1   2/2012

OTHER PUBLICATIONS

Forrer et al., "Fluorescence excitation and emission spectra of ALA-induced proptoporphyrin IX in normal and tumoral tissue of the human bladder," 1995, SPIE Proceeding, vol. 2324, pp. 84-88.*

(Continued)

*Primary Examiner* — Kiho Kim
(74) *Attorney, Agent, or Firm* — Ewers & Hasselmann PLLC

(57) ABSTRACT

An optical detection filter has a transmission spectrum for detecting fluorescence light of a plurality of different fluorescent dyes. In the range between 350 nm and 1000 nm, the transmission spectrum has a first stopband ($^PS1$) from $^P\lambda1$ to $^P\lambda2$, a first passband ($^PD1$) from $^P\lambda2$ to $^P\lambda3$, a second stopband ($^PS2$) from $^P\lambda3$ to $^P\lambda4$, a second passband ($^PD2$) from $^P\lambda4$ to $^P\lambda5$, a third stopband ($^PS3$) from $^P\lambda5$ to $^P\lambda6$, and a third passband ($^PD3$) from $^P\lambda6$ to $^P\lambda7$. The stopbands ($^PS1$, $^PS2$, $^PS3$) each have a mean transmittance of at most 0.01, typically at most 0.001 or at most 0.0001, and the passbands ($^PD1$, $^PD2$) each have a mean transmittance of at least 0.5, typically at least 0.8 or at least 0.9; wherein 350 nm$\leq ^P\lambda1 < ^P\lambda2 < ^P\lambda3 < ^P\lambda4 < ^P\lambda5 < ^P\lambda6 < ^P\lambda7 <$1000 nm.

48 Claims, 7 Drawing Sheets

(51) Int. Cl.
  *G01J 3/44* (2006.01)
  *G02B 21/06* (2006.01)
  *G02B 21/16* (2006.01)

(52) U.S. Cl.
  CPC .............. *G02B 21/06* (2013.01); *G02B 21/16* (2013.01); *G01N 2021/6471* (2013.01); *G01N 2201/06113* (2013.01)

(56) References Cited

U.S. PATENT DOCUMENTS

| | | | | |
|---|---|---|---|---|
| 5,127,730 | A * | 7/1992 | Brelje | G02B 21/0064 |
| | | | | 250/458.1 |
| 5,710,663 | A * | 1/1998 | Kawasaki | G02B 21/082 |
| | | | | 359/368 |
| 6,094,274 | A * | 7/2000 | Yokoi | G01N 21/6458 |
| | | | | 250/458.1 |
| 6,510,338 | B1 | 1/2003 | Irion et al. | |
| 6,603,552 | B1 * | 8/2003 | Cline | A61B 5/0059 |
| | | | | 356/39 |
| 2005/0151972 | A1 * | 7/2005 | Boege | G01N 21/253 |
| | | | | 356/417 |
| 2010/0044583 | A1 * | 2/2010 | Steffen | A61B 5/0059 |
| | | | | 250/458.1 |
| 2010/0110538 | A1 * | 5/2010 | Steffen | G02B 21/16 |
| | | | | 359/363 |
| 2012/0300294 | A1 | 11/2012 | Jess et al. | |
| 2012/0326055 | A1 * | 12/2012 | Wilson | A61B 5/0059 |
| | | | | 250/459.1 |
| 2013/0060106 | A1 * | 3/2013 | Aasmul | A61B 5/6849 |
| | | | | 600/316 |
| 2014/0211306 | A1 | 7/2014 | Jess et al. | |

OTHER PUBLICATIONS

Erdogan: "Optical Filters for Wavelength Selection in Fluorescence Instrumentation," Current Protocols in Cytrometry, John Wiley & Sons, Inc. ISBN: 978-0-471-14295-9, pp. 2.4.1-2.4.25, Apr. 1, 2011.
International Search Report issued in PCT/EP2016/001484, to which this application claims priority, and English-language translation thereof, dated Feb. 6, 2017.
Written Opinion issued in PCT/EP2016/001484, to which this application claims priority, dated Mar. 9, 2017.

* cited by examiner

OPTICAL FILTER SYSTEM AND FLUORESCENCE DETECTION SYSTEM

CROSS REFERENCE TO RELATED APPLICATIONS

This application is a continuation application of International Application No. PCT/EP2016/001484 filed on Sep. 1, 2016, and claims priority to German patent application 10 2015 011 429.8 filed on Sep. 1, 2015, both of which are hereby incorporated by reference in their entireties.

TECHNICAL FIELD

The present disclosure relates to optical filter systems for fluorescence observation, and fluorescence observation systems. In particular, the present disclosure relates to optical filter systems which are used in a fluorescence observation system for observing fluorescence of the fluorescent dyes protoporphyrin IX (PpIX), fluorescein, and indocyanine green (ICG).

BACKGROUND

The fluorescent dyes PpIX, fluorescein, and ICG are used in the medical field, in particular for staining biological material, for example blood cells, tumors or other tissue. If the tissue stained with a fluorescent dye is illuminated by light with a wavelength lying in the absorption spectrum of the fluorescent dye, the fluorescent dye emits fluorescence light. This fluorescence light may be detected in turn, as a result of which the region of a specific tissue stained with the fluorescent dye may be made visible and may be made distinguishable from the surrounding biological material. Frequently, a plurality of different fluorescent dyes are used for staining different biological materials within the scope of an operation. First of all, the surgeon may consider it advantageous to simultaneously observe different biological materials which were stained with different fluorescent dyes in each case. Secondly, it may likewise be advantageous to make certain biological materials visible by fluorescence light in a selective manner so as not to be distracted by a different fluorescence at the same time.

In the field of surgical applications, fluorescence observation systems are usually integrated in conventional surgical microscopes or provided by the latter. Therefore, as a rule, the fluorescence observation system is arranged over the region to be operated on and it should therefore be as compact as possible, i.e., take up little installation space, so as not to impede the surgeon. By way of example, conventional fluorescence observation systems are embodied as stereo microscopes, where the surgeon can view the operation region through eyepieces. A fluorescence image presented on a display may be overlaid onto the observation beam path of the stereo microscope with the aid of a further optical system, and so the surgeon is able to see the operation region and the fluorescence image at the same time.

In conventional fluorescence observation systems, use is frequently made of a single broadband light source which provides both the excitation light, i.e., the light for exciting the fluorescent dyes, and the illumination light, i.e., the light for producing an overview image. Usually, an illumination filter arranged in the beam path from the light source to an object region, in which the object that was stained with the fluorescent dyes is arranged, is required and it forms the intensity spectrum of the excitation light directed onto the object region and the intensity spectrum of the illumination light directed onto the object region. The illumination filter adopts the object of suitably adjusting the intensity ratios between the excitation light and the illumination light.

As a rule, it is not possible to simultaneously observe a plurality of fluorescences using conventional fluorescence observation systems since the employed filter system, consisting of the illumination filter and a detection filter that is arranged in the beam path from the object region to the eyepieces, is only optimized for a single fluorescent dye.

As shown schematically in FIG. 2A, the fluorescent dye protoporphyrin IX (PpIX) has an absorption spectrum which, between 350 nm and 430 nm, has a normalized absorption intensity of more than 0.2. The normalized absorption intensity is normalized to the maximum absorption intensity; i.e., the normalized absorption spectrum only has values of between 0 and 1. Therefore, the fluorescent dye PpIX may be efficiently excited in the range from 350 nm to 430 nm. The fluorescent dye has the maximum of the absorption at approximately 405 nm. The fluorescent dye PpIX emits fluorescence light in a spectral range from approximately 600 nm to 750 nm, with a main maximum of the emission intensity lying at 635 nm and a secondary maximum lying at approximately 705 nm.

As shown schematically in FIG. 3A, the fluorescent dye fluorescein has, between approximately 450 nm and 530 nm, a normalized absorption intensity of more than 0.2. Therefore, the fluorescent dye fluorescein can be excited well in this range. The absorption spectrum of fluorescein has a maximum at approximately 495 nm. The fluorescent dye fluorescein emits emission light in the range from approximately 490 nm to 650 nm. The maximum of the emission spectrum lies at approximately 520 nm.

As shown schematically in FIG. 5A, the fluorescent dye indocyanine green (ICG) has, between 700 nm and approximately 840 nm, a normalized absorption intensity of more than 0.2. Therefore, indocyanine green can be excited well in this range. The maximum of the absorption spectrum of indocyanine green lies at approximately 800 nm. The fluorescent dye indocyanine green emits emission light in the range from approximately 750 nm to 1000 nm. The maximum of the emission spectrum lies at approximately 835 nm.

SUMMARY

It is an object of the present disclosure to provide optical filter systems, which are configured to excite at least one fluorescent dye, and to detect the fluorescence light of the excited fluorescent dye. In particular, it is an object of the present disclosure to provide optical filter systems and fluorescence observation systems for observing PpIX, fluorescein, and ICG.

According to an exemplary embodiment, an optical filter system for observing fluorescence is provided, wherein the filter system comprises an illumination filter and a detection filter. The transmission spectrum of the illumination filter, in a wavelength range from 350 nm to 1000 nm, has a first stopband $^B S1$ from 350 nm to $^B \lambda 1$ with a mean transmittance of $^B TS1$, a first passband $^B D1$ from $^B \lambda 1$ to $^B \lambda 2$ with a mean transmittance of $^B TD1$, a second stopband $^B S2$ from $^B \lambda 2$ to $^B \lambda 3$ with a mean transmittance of $^B TS2$, a second passband $^B D2$ from $^B \lambda 3$ to $^B \lambda 4$ with a mean transmittance of $^B TD2$, and a third stopband $^B S3$ from $^B \lambda 4$ to $^B \lambda 5$ with a mean transmittance of $^B TS3$, where the following applies: 350 nm$\leq ^B \lambda 1 < ^B \lambda 2 < ^B \lambda 3 < ^B \lambda 4 < ^B \lambda 5 \leq$1000 nm.

The mean transmittance $^B TD1$ of the first passband $^B D1$ is greater than the mean transmittance $^B TS1$ of the first stopband $^B S1$ and greater than the mean transmittance $^B TS2$ of the second stopband $^B S2$. Further, the mean transmittance $^B TD2$ of the second passband $^B D2$ is greater than the mean transmittance $^B TS2$ of the second stopband $^B S2$ and greater than the mean transmittance $^B TS3$ of the third stopband $^B S3$.

Herein, the transmission spectrum denotes the ratio of the intensity of light at a wavelength $\lambda$ transmitted through the illumination filter to the intensity of the light at a wavelength $\lambda$ directed at the illumination filter within the wavelength range. Further, this ratio is referred to as transmittance $T(\lambda)$. Therefore, the transmission spectrum represents the wavelength-dependent transmittance within a wavelength range. In the case of the illumination filter, the transmission spectrum represents the transmittance in the wavelength range from 350 nm to 1000 nm.

Here, the mean transmittance $\overline{T}$ describes a mean value of the transmittances $T(\lambda)$ within a restricted wavelength range. By way of example, the mean transmittance $\overline{T}$ may be defined as:

$$\overline{T} = \frac{1}{\lambda^h - \lambda^l} \int_{\lambda^l}^{\lambda^h} T(\lambda) d\lambda.$$

The transmission spectrum of the detection filter, in the wavelength range from 350 nm to 1000 nm, has a first stopband $^D S1$ from 350 nm to $^D \lambda 1$ with a mean transmittance of $^D TS1$, a first passband $^D D1$ from $^D \lambda 1$ to $^D \lambda 2$ with a mean transmittance of $^D TD1$, a second stopband $^D S2$ from $^D \lambda 2$ to $^D \lambda 3$ with a mean transmittance of $^D TS2$, a second passband $^D D2$ from $^D \lambda 3$ to $^D \lambda 4$ with a mean transmittance of $^D TD2$, and a third stopband $^D S3$ from $^D \lambda 4$ to $^D \lambda 5$ with a mean transmittance of $^D TS3$, where the following applies: 350 nm$\leq^D \lambda 1 < ^D \lambda 2 < ^D \lambda 3 < ^D \lambda 4 < ^D \lambda 5 \leq$1000 nm.

The mean transmittance $^D TD1$ of the first passband $^D D1$ is greater than the mean transmittance $^D TS1$ of the first stopband $^D S1$ and greater than the mean transmittance $^D TS2$ of the second stopband $^D S2$. Further, the mean transmittance $^D TD2$ is greater than the mean transmittance $^D TS2$ of the second stopband $^D S2$ and greater than the mean transmittance $^D TS3$ of the third stopband $^D S3$.

In the nomenclature used herein, the superscript index denotes the detection filter with the letter "D" and the illumination filter with the letter "B". Stopbands are denoted by the letter "S" and passbands are denoted by the letter "D". The mean transmittances of stopbands are denoted by "TS" and the mean transmittances of passbands are denoted by "TD".

For a fluorescence observation of the fluorescent dye PpIX, the illumination filter of the optical filter system may be configured as follows:
 380 nm$\leq^B \lambda 1 \leq$400 nm; 410 nm$\leq^B \lambda 2 \leq$420 nm;
 425 nm$\leq^B \lambda 3 \leq$435 nm; 465 nm$\leq^B \lambda 4 \leq$485 nm;
 850 nm$\leq^B \lambda 5 \leq$1000 nm.

The detection filter fitting hereto may be configured as follows:
 425 nm$\leq^D \lambda 1 \leq$435 nm; 465 nm$\leq^D \lambda 2 \leq$485 nm;
 580 nm$\leq^D \lambda 3 \leq$620 nm; 650$\leq^D \lambda 4 \leq$770 nm;
 850 nm$\leq^D \lambda 5 \leq$1000 nm.
 where, in particular, $^D \lambda 4 \leq$720 nm or $^D \lambda 4 \leq$680 nm.

In particular, the first stopband $^D S1$ of the detection filter may, at least partly or else completely, include the first passband $^B D1$ of the illumination filter. As a result of this, the excitation light directed to an object for exciting the fluorescent dye PpIX may be suppressed by the detection filter. Further, the first passband $^D D1$ of the detection filter may, at least partly or else completely, include the second passband $^B D2$ of the illumination filter. As a result of this, the illumination light transmitted through the second passband $^B D2$ of the illumination filter may also be transmitted through the detection filter in order to be able to detect an overview image of the object region.

In particular, the following may apply for the mean transmittances of the stopbands and passbands of the illumination filter:
 $^B TS1<0.01$, typically $^B TS1<0.001$ or $^B TS1<0.0001$;
 $^B TD1>0.5$, typically $^B TD1>0.8$ or $^B TD1>0.9$;
 $^B TS2<0.1$, typically $^B TS2<0.05$ or $^B TS2<0.001$;
 $^B TD2>0.1$, typically $^B TD2>0.8$ or $^B TD2>0.9$;
 $^B TS3<0.01$, typically $^B TS3<0.001$ or $^B TS3<0.0001$.

Corresponding thereto, the following may apply for the mean transmittances of the stopbands and passbands of the detection filter:
 $^D TS1<0.01$, typically $^D TS1<0.001$ or $^D TS1<0.0001$;
 $^D TD1>0.5$, typically $^D TD1>0.8$ or $^D TD1>0.9$;
 $^D TS2<0.1$, typically $^D TS2<0.01$ or $^D TS2<0.001$;
 $^D TD2>0.5$, typically $^D TD2>0.8$ or $^D TD2>0.9$;
 $^D TS3<0.01$, typically $^D TS3<0.001$ or $^D TS3<0.0001$.

So as not to overlay illumination light, excitation light and/or ambient light on the emission light of the fluorescent dye PpIX, a range from 600 nm to 750 nm within the third stopband $^B S3$ of the illumination filter may have a mean transmittance of at most 0.001, typically at most 0.0001. The region within the third stopband $^B S3$ of the illumination filter may, at least partly or else completely, include the emission range of PpIX, i.e., the spectral range in which the fluorescent dye PpIX emits fluorescence light.

The following may apply for the illumination filter for the purposes of exciting and detecting fluorescein:
 420 nm$\leq^B \lambda 1 \leq$440 nm; 480 nm$\leq^B \lambda 2 \leq$520 nm;
 600 nm$\leq^B \lambda 3 \leq$640 nm; 680 nm$\leq^B \lambda 4 \leq$720 nm;
 850 nm$\leq^B \lambda 5 \leq$1000 nm, and
 $^B TD2>0.1$.

Corresponding hereto, the following may apply for the detection filter:
 475 nm$\leq^D \lambda 1 \leq$495 nm; 500 nm$\leq^D \lambda 2 \leq$505 nm;
 505 nm$\leq^D \lambda 3 \leq$515 nm; 680 nm$\leq^D \lambda 4 \leq$720 nm;
 850 nm$\leq^D \lambda 5 \leq$1000 nm.
 wherein, in particular, the following applies: 490 nm$\leq^D \lambda 1$.

As result of this configuration of the illumination filter and detection filter, the first passband $^B D1$ of the illumination filter includes at least part of the absorption spectrum of fluorescein such that excitation light can efficiently excite the fluorescent dye fluorescein. Further, the second stopband $^B S2$ of the illumination filter suppresses light directed to the illumination filter in a spectral range which substantially corresponds to the emission range of fluorescein. The second passband $^B D2$ of the illumination filter may be used, just like a spectral range in the first passband $^B D1$ of the illumination filter, to direct illumination light onto an object region. The first stopband $^B S1$ and the third stopband $^B S3$ of the illumination filter suppress ambient light.

The first passband $^D D1$ of the detection filter includes a part of the first passband $^B D1$ of the illumination filter such that some of the excitation light and/or illumination light which is transmitted through the first passband $^D D1$ of the illumination filter is also transmitted through the detection filter. The second passband $^B D1$ of the detection filter includes both at least a part of the emission range of fluorescein and at least a part of the second passband $^B D2$ of the illumination filter. As a result of this, it is possible to transmit through the detection filter and detect both illumination light, which is transmitted through the second passband $^{B}D2$ of the illumination filter and fluorescence light of fluorescein.

In particular, the following may apply for the mean transmittances of the stopbands and passbands of the illumination filter:

$^{B}TS1<0.1$, typically $^{B}TS1<0.01$ or $^{B}TS1<0.001$;
$^{B}TD1>0.5$, typically $^{B}TD1>0.8$ or $^{B}TD1>0.9$;
$^{B}TS2<0.01$, typically $^{B}TS2<0.001$ or $^{B}TS2<0.0001$;
$^{B}TD2>0.01$, typically $^{B}TD2>0.1$ or $^{B}TD2>0.8$;
$^{B}TS3<0.01$, typically $^{B}TS3<0.001$ or $^{B}TS3<0.0001$.

Corresponding thereto, the following may apply for the mean transmittances of the stopbands and passbands of the detection filter:

$^{D}TS1<0.001$, typically $^{D}TS1<0.0001$ or $^{D}TS1<0.00001$; $0.1>^{D}TD1>0.001$;
$^{D}TS2<0.001$, typically $^{D}TS2<0.0001$;
$^{D}TD2>0.1$, typically $^{D}TD2>0.5$ or $^{D}TD2>0.8$;
$^{D}TS3<0.01$, typically $^{D}TS3<0.001$ or $^{D}TS3<0.0001$.

According to a further exemplary embodiment of an optical filter system, it is possible to excite both the fluorescent dye PpIX and the fluorescent dye fluorescein, and detect the fluorescence light thereof. By way of example, the illumination filter of this optical filter system may be configured by:

380 nm$\leq^{B}\lambda 1\leq$400 nm; 410 nm$\leq^{B}\lambda 2\leq$420 nm;
440 nm$\leq^{B}\lambda 3\leq$460 nm; 490 nm$\leq^{B}\lambda 4\leq$505 nm;
850 nm$\leq^{B}\lambda 5\leq$1000 nm.

In this respect, the following may correspondingly apply for the detection filter:

440 nm$\leq^{D}\lambda 1\leq$460 nm; 490 nm$\leq^{D}\lambda 2\leq$500 nm;
505 nm$\leq^{D}\lambda 3\leq$515 nm; 650 nm$\leq^{D}\lambda 4\leq$770 nm;
850 nm$\leq^{D}\lambda 5\leq$1000 nm.

wherein, in particular, the following applies: $^{D}\lambda 2<^{B}\lambda 2$.

In this embodiment, the first passband $^{B}D1$ of the illumination filter includes at least a part of the absorption spectrum of PpIX. As a result of this, the fluorescent dye PpIX may be excited by excitation light transmitted through the first passband $^{B}D1$ of the illumination filter. The second passband $^{B}D2$ of the illumination filter includes at least a part of the absorption spectrum of fluorescein, with the part typically lying outside of the emission range of fluorescein or lying in such a spectral range in which the emission spectrum of fluorescein has low values, for example values <0.2. Between the first passband $^{B}D1$ and the second passband $^{B}D2$ of the illumination filter, the second stopband $^{B}S2$ of the illumination filter suppresses crosstalk between excitation light for exciting fluorescein and excitation light for exciting PpIX.

In a range from $^{B}\lambda 3$ to $^{B}\lambda 3'$, in which the absorption spectrum of fluorescein has small values, illumination light may be transmitted through the illumination filter, it being possible to use said illumination light to produce an overview image in the blue spectral range. The range $^{B}\lambda 3$ to $^{B}\lambda 3'$ has a mean transmittance of at least $^{B}W1$ and a further range from $^{B}\lambda 3'$ to $^{B}\lambda 4$ has a mean transmittance of at least $^{B}W2$. Since the range from $^{B}\lambda 3'$ to $^{B}\lambda 4$ is used to transmit excitation light for exciting fluorescein, $^{B}W2$ may typically have high values. In particular, the following applies: $^{B}W2>0.5$, typically >0.8 or >0.9. In particular, $^{B}W2>^{B}W1$ applies. Typically, the following applies for $^{B}\lambda 3'$: 470 nm$\leq^{B}\lambda 3'\leq$490 nm. The first stopband $^{B}S1$ and the third stopband $^{B}S3$ of the illumination filter serve to suppress ambient light.

In particular, the following may apply for the mean transmittances of the stopbands and passbands of the illumination filter:

$^{B}TS1<0.01$, typically $^{B}TS1<0.001$ or $^{B}TS1<0.0001$;
$^{B}TD1>0.5$, typically $^{B}TD1>0.8$ or $^{B}TD1>0.9$;
$^{B}TS2<0.1$, typically $^{B}TS2<0.01$ or $^{B}TS2<0.001$;
$^{B}TD2>0.5$, typically $^{B}TD2>0.8$ or $^{B}TD2>0.9$;
$^{B}TS3<0.01$, typically $^{B}TS3<0.001$ or $^{B}TS3<0.0001$.

According to the aforementioned configuration, the second passband $^{C}D2$ of the detection filter is suitable for transmitting fluorescence light of the fluorescent dyes PpIX and fluorescein well. The first passband $^{L}D1$ of the detection filter is configured to transmit illumination light. In particular, a range from $^{D}\lambda 1$ to $^{D}\lambda 1'$ has a mean transmittance of at least $^{D}W1$, wherein this range may at least partly, typically completely, include the range from $^{B}\lambda 3$ to $^{B}\lambda 3'$ of the illumination filter, as a result of which the illumination light can be transmitted well through the detection filter. The first passband $^{D}D1$ of the detection filter may further include a range from $^{D}\lambda 1'$ to $^{D2}$ with a mean transmittance of at least $^{D}W2$, wherein, in particular, the following applies: $^{D}W2<^{D}W1$, where, in particular, $^{D}W2$ is at most 0.05 or 0.01. The following may apply for $^{D}\lambda 1'$: 470 nm$\leq^{D}\lambda 1'\leq$490 nm.

The second passband $^{D}D2$ of the detection filter may include a range from $^{D}\lambda 3$ to $^{D}\lambda 3'$ with a mean transmittance of $^{D}W3$ and a range from $^{D}\lambda 3'$ to $^{D}\lambda 4$ with a mean transmittance of $^{D}W4$. The mean transmittances $^{D}W3$ and $^{D}W4$ may be selected depending on properties of the fluorescent dyes PpIX and fluorescein. What may be achieved in this way is that, for example, fluorescence light of the two fluorescent dyes has similar emission intensities at a given excitation.

In particular, the following may apply for the mean transmittances of the detection filter:

$^{D}TS1<0.01$, typically $^{D}TS1<0.001$ or $^{D}TS1<0.0001$;
$^{D}TD1>0.1$, typically $^{D}TD1>0.5$ or $^{D}TD1>0.8$;
$^{D}TS2<0.1$, typically $^{D}TS2<0.01$ or $^{D}TS2<0.001$;
$^{D}TD2>0.5$, typically $^{D}TD2>0.8$ or $^{D}TD2>0.9$;
$^{D}TS3<0.01$, typically $^{D}TS3<0.001$ or $^{D}TS3<0.0001$.

For the purposes of exciting indocyanine green and for detecting fluorescence light of indocyanine green, an optical filter system is proposed, wherein the following may apply for the illumination filter thereof:

380 nm$\leq^{B}\lambda 1\leq$420 nm; 680 nm$\leq^{B}\lambda 2\leq$720 nm;
750 nm$\leq^{B}\lambda 3\leq$790 nm; 810 nm$\leq^{B}\lambda 4\leq$815 nm;
950 nm$\leq^{B}\lambda 5\leq$1000 nm.

Corresponding hereto, the following may apply for the detection filter:

380 nm$\leq^{D}\lambda 1\leq$420 nm; 680 nm$\leq^{D}\lambda 2\leq$720 nm;
$^{B}\lambda 4\leq^{D}\lambda 3\leq^{B}\lambda 4+10$ nm; 900 nm$\leq^{D}\lambda 4\leq$940 nm;
940 nm$\leq^{B}\lambda 5\leq$1000 nm.

The first passband $^{B}D1$ of the illumination filter, which substantially comprises the range of visible light, may be used for illuminating the object region. The second passband $^{B}D2$ of the illumination filter serves to transmit excitation light for exciting indocyanine green. In order to delimit illumination light from excitation light, the second stopband $^{B}S2$ of the illumination filter has a low mean transmittance $^{B}TS2$. The first stopband $^{B}S1$ and the third stopband $^{B}S3$ of the illumination filter are configured to suppress ambient light.

In particular, the following may apply for the mean transmittances of the stopbands and passbands of the illumination filter:

$^{B}TS1<0.1$, typically $^{B}TS1<0.01$ or $^{B}TS1<0.001$;
$^{B}TD1>0.5$, typically $^{B}TD1>0.8$ or $^{B}TD1>0.9$;

$^B$TS2<0.1, typically $^B$TS2<0.01 or $^B$TS2<0.001;
$^B$TD2>0.5, typically $^B$TD2>0.8 or $^B$TD2>0.9;
$^B$TS3<0.1, typically $^B$TS3<0.01 or $^B$TS3<0.001.

The detection filter has the first passband $^D$D1, which includes substantially the same spectral range as the first passband $^B$D1 of the illumination filter. In particular, the first passband $^D$D1 of the detection filter may include the first passband $^B$D1 of the illumination filter.

In order to suppress excitation light which is transmitted by the second passband $^B$D2 of the illumination filter, the second stopband $^D$S2 of the detection filter includes a range from $^D\lambda 2'$ to $^D\lambda 3$, which has a mean transmittance of at most 0.01, typically at most 0.001. The following may apply for $^D\lambda 2'$: 760 nm $\leq {}^D\lambda 2' \leq$ 780 nm. In particular, $^D\lambda 2'$ may be selected in such a way that the range from $^D\lambda 2'$ to $^D\lambda 3$ includes the second passband $^B$D2 of the illumination filter.

The following may apply for the mean transmittances of the stopbands and passbands of the detection filter:
$^D$TS1<0.01, typically $^D$TS1<0.001 or $^D$TS1<0.0001;
$^D$TD1>0.5, typically $^D$TD1>0.8 or $^D$TD1>0.9;
$^D$TS2<0.1, typically $^D$TS2<0.01 or $^D$TS2<0.001 or $^D$TS2<0.0001;
$^D$TD2>0.5, typically $^D$TD2>0.8 or $^D$TD2>0.9;
$^D$TS3<0.1, typically $^D$TS3<0.01 or $^D$TS3<0.001.

According to a further exemplary embodiment of an optical filter system for observing fluorescence, in particular of PpIX, the optical filter system comprises an illumination filter and a detection filter, wherein the transmission spectrum of the illumination filter, in a wavelength range from 350 nm to 1000 nm, has a first stopband $^B$S1 from 350 nm to $^B\lambda 1$ with a mean transmittance of $^B$TS1, a first passband $^B$D1 from $^B\lambda 1$ to $^B\lambda 2$ with a mean transmittance of $^B$TD1, a second stopband $^B$S2 from $^B\lambda 2$ to $^B\lambda 3$ with a mean transmittance of $^B$TS2, a second passband $^B$D2 from $^B\lambda 3$ to $^B\lambda 4$ with a mean transmittance of $^B$TD2, and a third stopband $^B$S3 from $^B\lambda 4$ to $^B\lambda 5$ with a mean transmittance of $^B$TS3, wherein the following applies: 350 nm $\leq {}^B\lambda 1 < {}^B\lambda 2 < {}^B\lambda 3 < {}^B\lambda 4 < {}^B\lambda 5 \leq$ 1000 nm. Moreover, the mean transmittance $^B$TD1 of the first passband $^B$D1 is greater than the mean transmittance $^B$TS1 of the first stopband $^B$S1 and greater than the mean transmittance $^B$TS2 of the second stopband $^B$S2. Moreover, the mean transmittance $^B$TD2 of the second passband $^B$D2 is greater than the mean transmittance $^B$TS2 of the second stopband $^B$S2 and greater than the mean transmittance $^B$TS3 of the third stopband $^B$S3.

The transmission spectrum of the detection filter has, in the wavelength range from 350 nm to 1000 nm, a first stopband $^D$S1 from 350 nm to $^D\lambda 1$ with a mean transmittance of $^D$TS1, a first passband $^D$D1 from $^D\lambda 1$ to $^D\lambda 2$ with a mean transmittance of $^D$TD1 and a second stopband $^D$S2 from $^D\lambda 2$ to $^D\lambda 3$ with a mean transmittance of $^D$TS2, wherein the following applies: 350 nm $\leq {}^D\lambda 1 < {}^D\lambda 2 < {}^D\lambda 3 \leq$ 1000 nm. The mean transmittance $^D$TD1 of the first passband $^D$D1 is greater than the mean transmittance $^D$TS1 of the first stopband $^D$S1 and greater than the mean transmittance $^D$TS2 of the second stopband $^D$S2.

For the purposes of exciting the fluorescent dye PpIX and for detecting the fluorescence light of PpIX, and for the purposes of detecting an overview image in the visible spectral range, the optical filter system may be configured as follows:

By way of example, the illumination filter may be configured by:
380 nm $\leq {}^B\lambda 1 \leq$ 400 nm; 410 nm $\leq {}^B\lambda 2 \leq$ 420 nm;
440 nm $\leq {}^B\lambda 3 \leq$ 460 nm; 600 nm $\leq {}^B\lambda 4 \leq$ 800 nm;
950 nm $\leq {}^B\lambda 5 \leq$ 1000 nm.

By way of example, the detection filter may be configured by:
$^B\lambda 3 - 5$ nm $\leq {}^D\lambda 1 \leq {}^B\lambda 3 + 5$ nm; 600 nm $\leq {}^D\lambda 2 \leq$ 800 nm,
wherein, in particular, the first passband $^D$D1 of the detection filter includes the second passband $^B$D2 of the illumination filter or wherein, in particular, the following applies: $^D\lambda 2 \leq$ 720 nm or $^D\lambda 2 \leq$ 680 nm.

In this configuration, the first passband $^B$D1 of the illumination filter is configured to transmit excitation light for exciting PpIX. In addition to the emission range of PpIX, the second passband $^B$D2 includes further regions of the visible spectral range in order to be able to transmit illumination light onto the object region. In order to separate excitation light and illumination light, the second stopband $^B$S2 of the illumination filter has a low mean transmittance $^B$TS2. The first stopband $^B$S1 and the third stopband $^B$S3 of the illumination filter serve to suppress ambient light.

In particular, the following may apply for the mean transmittances of the stopbands and passbands of the illumination filter:
$^B$TS1<0.01, typically $^B$TS1<0.001 or $^B$TS1<0.0001;
$^B$TD1>0.5, typically $^B$TD1>0.8 or $^B$TD1>0.9;
$^B$TS2<0.1, typically $^B$TS2<0.01;
$^B$TD2>0.5, typically $^B$TD2>0.8 or $^B$TD2>0.9;
$^B$TS3<0.01, typically $^B$TS3<0.001 or $^B$TS3<0.0001.

The first passband $^D$D1 of the detection filter is configured to transmit the second passband $^B$D2 of the illumination filter, as a result of which both illumination light and emission light of PpIX can be transmitted through the detection filter. A first range from $^D\lambda 1$ to $^D\lambda 1'$ has a mean transmittance of at least $^D$W1 and a further range from $^D\lambda 1'$ to $^D\lambda 2$ has a mean transmittance of at least $^D$W2. In particular, the following may apply: $^D$W2 > $^D$W1. In order to be able to efficiently transmit the fluorescence light of PpIX, the value $^D$W2 may have a particularly high value. By way of example, the following applies: $^D$W2>0.5, $^D$W2>0.8 or $^D$W2>0.9.

The following may apply for the mean transmittances of the stopbands and passband of the detection filter:
$^D$TS1<0.01, typically $^D$TS1<0.001 or $^D$TS1<0.0001;
$^D$TD1>0.5, typically $^D$TD1>0.7 or $^D$TD1>0.8;
$^D$TS2<0.01, typically $^D$TS2<0.001 or $^D$TS2<0.0001.

According to a development of this optical filter system, $^B\lambda 4$ may be selected such that the following applies: $^B\lambda 4 \leq$ 600 nm. In this case, the illumination filter suppresses light within the emission range of PpIX. Consequently, the emission range is not overlaid with illumination light or excitation light.

A detection filter, by means of which it is possible to detect fluorescence light of the three fluorescent dyes PpIX, fluorescein, and indocyanine green and suitably suppress excitation light, will be described next. The optical detection filter has a transmission spectrum which, between 350 nm and 1000 nm, has a first stopband $^D$S1 from $^D\lambda 1$ to $^D\lambda 2$, a first passband $^D$D1 from $^D\lambda 2$ to $^D\lambda 3$, a second stopband $^D$S2 from $^D\lambda 3$ to $^D\lambda 4$, a second passband $^D$D2 from $^D\lambda 4$ to $^D\lambda 5$, a third stopband $^D$S3 from $^D\lambda 5$ to $^D\lambda 6$, and a third passband $^D$D3 from $^D\lambda 6$ to $^D\lambda 7$, wherein the stopbands each have a mean transmittance of at most 0.01, typically at most 0.001 or at most 0.0001, and wherein the passbands each have a mean transmittance of at least 0.5, typically at least 0.8 or at least 0.9, and wherein the following applies: 350 nm $\leq {}^D\lambda 1 < {}^D\lambda 2 < {}^D\lambda 3 < {}^D\lambda 4 < {}^D\lambda 5 < {}^D\lambda 6 < {}^D\lambda 7 <$ 1000 nm.

For the purposes of suppressing excitation light for the three fluorescent dyes PpIX, fluorescein, and indocyanine green and for the purposes of detecting the fluorescence light thereof, the detection filter may be configured by:

350 nm≤$^D\lambda1$≤400 nm; 410 nm≤$^D\lambda2$≤435 nm;
465 nm≤$^D\lambda3$≤475 nm; 495 nm≤$^D\lambda4$≤515 nm;
765 nm≤$^D\lambda5$≤775 nm; 795 nm≤$^D\lambda6$≤825 nm;
910 nm≤$^D\lambda7$≤930 nm.

The first stopband $^DS1$ of the detection filter accordingly includes the spectral range in which the absorption spectrum of PpIX has high values, i.e., the spectral range of the excitation light used to excite PpIX. The second stopband $^DS2$ includes a spectral range in which the absorption spectrum of fluorescein has high values, i.e., the spectral range of the excitation light used to excite fluorescein. The third stopband $^DS3$ of the detection filter includes a spectral range in which the absorption spectrum of ICG has high values, i.e., the spectral range of the excitation light used to excite ICG. By way of example, 0.1, 0.2 or 0.5 may count as high values, wherein the assumption of normalized absorption spectra and absorption intensities should be made in each case. The optional fourth stopband $^DS4$ of the detection filter serves to suppress ambient light.

The first passband $^LD1$ of the detection filter includes a spectral range within which, for example, blue excitation light may be directed onto the object region for the purposes of producing an overview image and may be transmitted by the detection filter. The second passband $^DD2$ of the detection filter includes both at least a part of the emission range of fluorescein and at least a part of the emission range of PpIX. Therefore, fluorescence light of these two fluorescent dyes may be transmitted through the second passband $^DD2$ of the detection filter and may be detected. The third passband $^DD3$ of the detection filter includes at least a part of the emission range of ICG such that fluorescence light from ICG may be transmitted through the third passband $^DD3$ and may be detected.

So that the fluorescence light of fluorescein and PpIX can be detected well, it is possible for a spectral range from 510 nm to 750 nm within the second passband $^DD2$ of the detection filter to have a mean transmittance of at least 0.9.

Suitable light sources for exciting the three fluorescent dyes are lasers with central emission wavelengths of 405 nm and 488 nm and 785 nm, respectively. If a laser is used to excite a fluorescent dye, the stopband of the detection filter which includes the emission wavelength of the laser may be selected to be narrowband. By contrast, if light-emitting diodes with a broader emission spectrum are used for excitation purposes, the stopbands should accordingly be selected to be more broadband.

According to an exemplary embodiment, the first stopband $^DS1$ includes the spectral range from 400 nm to 410 nm, in particular the spectral range from 385 nm to 435 nm. Further, or alternatively, the second stopband $^DS2$ may include the spectral range from 475 nm to 495 nm, in particular the spectral range from 465 nm to 515 nm. Further, or alternatively, the third stopband DS3 may include the spectral range from 775 nm to 795 nm, in particular the spectral range from 775 nm to 825 nm.

According to exemplary embodiments, the mean transmittance of a passband is at least 5 times, in particular at least 10 times or at least 100 times greater than the mean transmittances of the stopbands spectrally adjoining the passband. This may apply to the illumination and/or detection filters described herein.

The above-described optical filter systems and the detection filter for detecting the three fluorescent dyes PpIX, fluorescein, and indocyanine green may be used in a fluorescence observation system comprising: a light production system, which is configured to produce excitation light for exciting fluorescence and illumination light that differs from the excitation light, and direct said light onto an object region, a spatially resolving camera for detecting an image of the object region, and an optical filter system or the detection filter for detecting PpIX, fluorescein, and indocyanine green. If use is made of one of the optical filter systems explained above, the illumination filter is arranged in a beam path between the light production system and the object region and the detection filter is arranged in a beam path between the object region and the camera. By contrast, if the detection filter is used to detect PpIX, fluorescein, and indocyanine green, it is possible to dispense with the illumination filter.

The light production system may comprise a plurality of light sources, wherein the intensity of the light produced by each of the light sources is adjustable in each case. As a result of this, it is possible to adjust the intensities of the fluorescence light of the various fluorescent dyes and the intensity of the illumination light and to match these to one another.

According to an exemplary embodiment, the light sources of the light production system are configured to emit excitation light substantially only within the stopbands of the detection filter. Under the further precondition that the illumination light spectrum likewise has a sufficiently narrowband selection, this allows the illumination filter to be dispensed with. Light sources emit substantially only within a stopband if the maximum intensity of the light produced by the light source outside of the stopband has a value that is less than 1%, in particular less than 0.1% or less than 0.01% of the maximum intensity of the light produced by the light source within the stopband.

In particular, the light production system for producing excitation light may comprise:

a laser with a central emission wavelength of $\Lambda1$ or a narrowband violet LED with a central emission wavelength of $\Lambda2$, wherein 405 nm−$\Delta\Lambda_{Laser}$≤$\Lambda1$≤405 nm+$\Delta\Lambda_{Laser}$, where $\Delta\Lambda_{Laser}$=5 nm;

410 nm−$\Delta\Lambda_{LED}$≤$\Lambda2$≤410 nm+$\Delta\Lambda_{LED}$, where $\Delta\Lambda_{LED}$=20 nm;

and/or a laser with a central emission wavelength of $\Lambda3$ or a narrowband cyan LED with a central emission wavelength of $\Lambda4$, wherein 488 nm−$\Delta\Lambda_{Laser}$≤$\Lambda3$≤488 nm+$\Delta\Lambda_{Laser}$, where $\Delta\Lambda_{Laser}$=5 nm;

490 nm−$\Delta\Lambda_{LED}$≤$\Lambda4$≤490 nm+$\Delta\Lambda_{LED}$, where $\Delta\Lambda_{LED}$=20 nm;

and/or a laser with a central emission wavelength of $\Lambda5$ or a narrowband IR LED with a central emission wavelength of $\Lambda6$, wherein 785 nm−$\Delta\Lambda_{Laser}$≤$\Lambda5$≤785 nm+$\Delta\Lambda_{Laser}$, where $\Delta\Lambda_{Laser}$=5 nm;

800 nm−$\Delta\Lambda_{LED}$≤$\Lambda6$≤800 nm+$\Delta\Lambda_{LED}$, where $\Delta\Lambda_{LED}$=20 nm.

In order to produce illumination light, the light production system may, for example, comprise: a narrowband blue LED with a central emission wavelength in the range from 450 nm−$\Delta\Lambda_{LED}$ to 450 nm+$\Delta\Lambda_{LED}$; $\Delta\Lambda_{LED}$=20 nm; and/or a broadband LED which emits light in the spectral range from 400 nm to 700 nm; and/or a narrowband red LED with a central emission wavelength in the range from 660 nm−$\Delta\Lambda_{LED}$ to 660 nm+$\Delta\Lambda_{LED}$; $\Delta\Lambda_{LED}$=20 nm; and/or a narrowband green LED with a central emission wavelength in the range from 540 nm−$\Delta\Lambda_{LED}$ to 540 nm+$\Delta\Lambda_{LED}$; $\Delta\Lambda_{LED}$=20 nm. Further, parts of the excitation light may also serve as illumination light.

In order to excite the fluorescent dye PpIX, the laser with the central emission wavelength Λ1 or the narrowband violet LED with the central emission wavelength Λ2 may be used, for example. In order to excite fluorescein, the laser with the central emission wavelength Λ3 or the narrowband cyan LED with the central emission wavelength Λ4 may be used, for example. In order to excite indocyanine green, the laser with the central emission wavelength Λ5 or the narrowband IR LED with the central emission wavelength Λ6 may be used, for example. In order to simultaneously excite PpIX and fluorescein, it is possible to use a single light source with a central emission wavelength within a spectral range, the spectral range including an overlap of the absorption spectra of PpIX and fluorescein, instead of two different light sources. As a result of a suitable selection of the central emission wavelength, this may further be used to control the ratio of the excitation intensities of the two fluorescent dyes, as a result of which, further, it is possible to control the fluorescence light intensities of the two fluorescent dyes. In particular, this allows the fluorescence light intensities to be adapted with respect to one another.

According to an exemplary embodiment of the fluorescence observation system, the camera is configured to record a first image of the object region while the excitation light and the illumination light are directed onto the object region.

In this embodiment, the object region is simultaneously illuminated by excitation light and illumination light. Therefore, the object region reflects excitation light and illumination light and emits fluorescence light. Illumination light and fluorescence light transmitted through the detection filter is detected simultaneously by the camera.

According to an exemplary embodiment herein, the camera is further configured to record a second image of the object region while only the excitation light or only the illumination light is directed onto the object region.

In this embodiment, it is either only the excitation light or only the illumination light that is directed onto the illumination filter and, accordingly, onto the object region when the second image of the object region is recorded.

Accordingly, the first image is formed by both reflected illumination light and fluorescence light whereas the second image is only produced from reflected illumination light or excitation light. Consequently, it is possible to produce an image formed only by illumination light and an image formed only by fluorescence light by way of suitable processing of the two images.

According to an exemplary embodiment, the camera is configured to record a first image of the object region while only the excitation light is directed onto the object region and to record a second image of the object region while only the illumination light is directed onto the object region.

In this embodiment, the first image is formed only by fluorescence light, with a suitable suppression of excitation light in the detection filter being assumed, said suppression being suitable according to the explained optical filter systems and the detection filter. The second image is formed only by reflected illumination light.

The first image and the second image can be processed further for presentation purposes; by way of example, the fluorescence light image, i.e., the image formed by fluorescence light, may be overlaid on the overview image and be suitably prepared for an improved perception. Further, regions of the fluorescence light image may be represented, for example, by shadows or edges.

The fluorescence observation system may be operated in a plurality of modes of operation, which are explained below.

In a first mode of operation of the fluorescence observation system, the laser with the central emission wavelength Λ1, 405 nm−$\Delta\Lambda_{Laser}$≤Λ1≤405 nm+$\Delta\Lambda_{Laser}$, $\Delta\Lambda_{Laser}$=5 nm, or the narrowband violet LED with the central emission wavelength Λ2, 410 nm−$\Delta\Lambda_{LED}$≤Λ2≤410 nm+$\Delta\Lambda_{LED}$, $\Delta\Lambda_{LED}$=20 nm, is used to produce the excitation light and the narrowband blue LED with the central emission wavelength in the range from 450 nm−$\Delta\Lambda_{LED}$ to 450 nm+$\Delta\Lambda_{LED}$, $\Delta\Lambda_{LED}$=20 nm, is used to produce the illumination light. This mode of operation is suitable, in particular, for exciting and observing PpIX and for producing a bluish overview image.

In a second mode of operation of the fluorescence observation system, the laser with the central emission wavelength Λ3, 488 nm−$\Delta\Lambda_{Laser}$≤Λ3≤488 nm+$\Delta\Lambda_{Laser}$, $\Delta\Lambda_{Laser}$=5 nm, or the narrowband cyan LED with the central emission wavelength Λ4, 490 nm−$\Delta\Lambda_{LED}$≤Λ4≤490 nm+$\Delta\Lambda_{LED}$, $\Delta\Lambda_{LED}$=20 nm, is used to produce the excitation light and the red LED with a central emission wavelength in the range from 660 nm−$\Delta\Lambda_{LED}$ to 660 nm+$\Delta\Lambda_{LED}$, $\Delta\Lambda_{LED}$=20 nm, is used to produce the illumination light. This mode of operation is suitable, in particular, for exciting and observing fluorescein and for producing a whitish overview image.

In a third mode of operation of the fluorescence observation system, the laser with the central emission wavelength Λ1 or the narrowband violet LED and the laser with the central emission wavelength Λ3 or the narrowband blue LED is used to produce the excitation light and the narrowband blue LED with the central emission wavelength in the range from 450 nm−$\Delta\Lambda_{LED}$ to 450 nm+$\Delta\Lambda_{LED}$, $\Delta\Lambda_{LED}$=20 nm, is used to produce to illumination light. This mode of operation is suitable, in particular, for simultaneously exciting and observing PpIX and fluorescein and for producing a bluish overview image. Instead of using a plurality of light sources, it is also possible to use only one light source for producing the excitation light, with the emission spectrum of the one light source being able to excite both PpIX and fluorescein.

In a fourth mode of operation of the fluorescence observation system, the laser with the central emission wavelength Λ5, 785 nm−$\Delta\Lambda_{Laser}$≤Λ5≤785 nm+$\Delta\Lambda_{Laser}$, $\Delta\Lambda_{Laser}$=5 nm, or the narrowband IR LED with the central emission wavelength Λ6, 800 nm−$\Delta\Lambda_{LED}$≤Λ6≤800 nm+$\Delta\Lambda_{LED}$, $\Delta\Lambda_{LED}$=20 nm, is used to produce the excitation light and the broadband LED which emits light in the spectral range from 400 nm to 700 nm is used to produce the illumination light. This mode of operation is suitable, in particular, for exciting and observing ICG and for producing a whitish overview image.

Each of the first mode of operation to fourth mode of operation allow both fluorescence light and reflected illumination light to be detected at the same time without spectrally overlapping one another. Therefore, there is no need for computational correction of the recorded image and the latter shows the overview image in a state of direct overlay with the fluorescence light image.

In a fifth mode of operation of the fluorescence observation system, the laser with the central emission wavelength of Λ1, 405 nm−$\Delta\Lambda_{Laser}$≤Λ1≤405 nm+$\Delta\Lambda_{Laser}$, $\Delta\Lambda_{Laser}$=5 nm, or the narrowband violet LED with the central emission wavelength of Λ2, 410 nm−$\Delta\Lambda_{LED}$≤Λ2≤410 nm+$\Delta\Lambda_{LED}$, $\Delta\Lambda_{LED}$=20 nm, is used to produce the excitation light, and, further or alternatively, the laser with the central emission wavelength of Λ3, 488 nm−ΔΛ$_{Laser}$≤Λ3≤488 nm+ΔΛ$_{Laser}$, ΔΛ$_{Laser}$=5 nm, or the narrowband cyan LED with the central emission wavelength of Λ4, 490 nm−ΔΛ$_{LED}$≤Λ4≤490 nm+ΔΛ$_{LED}$, ΔΛ$_{LED}$=20 nm, is used to produce the excitation light, and the broadband LED which emits light in the spectral range from 400 nm to 700 nm is used to produce the illumination light. This mode of operation is suitable, in particular, for exciting and observing PpIX and/or fluorescein and for producing a whitish overview image.

The illumination and detection filters described herein may be formed in each case by suitable layering of a multiplicity of materials with different refractive indices according to known methods.

BRIEF DESCRIPTION OF THE DRAWINGS

The invention will now be described with reference to the drawings wherein.

DESCRIPTION OF EXEMPLARY EMBODIMENTS

Figure 1:
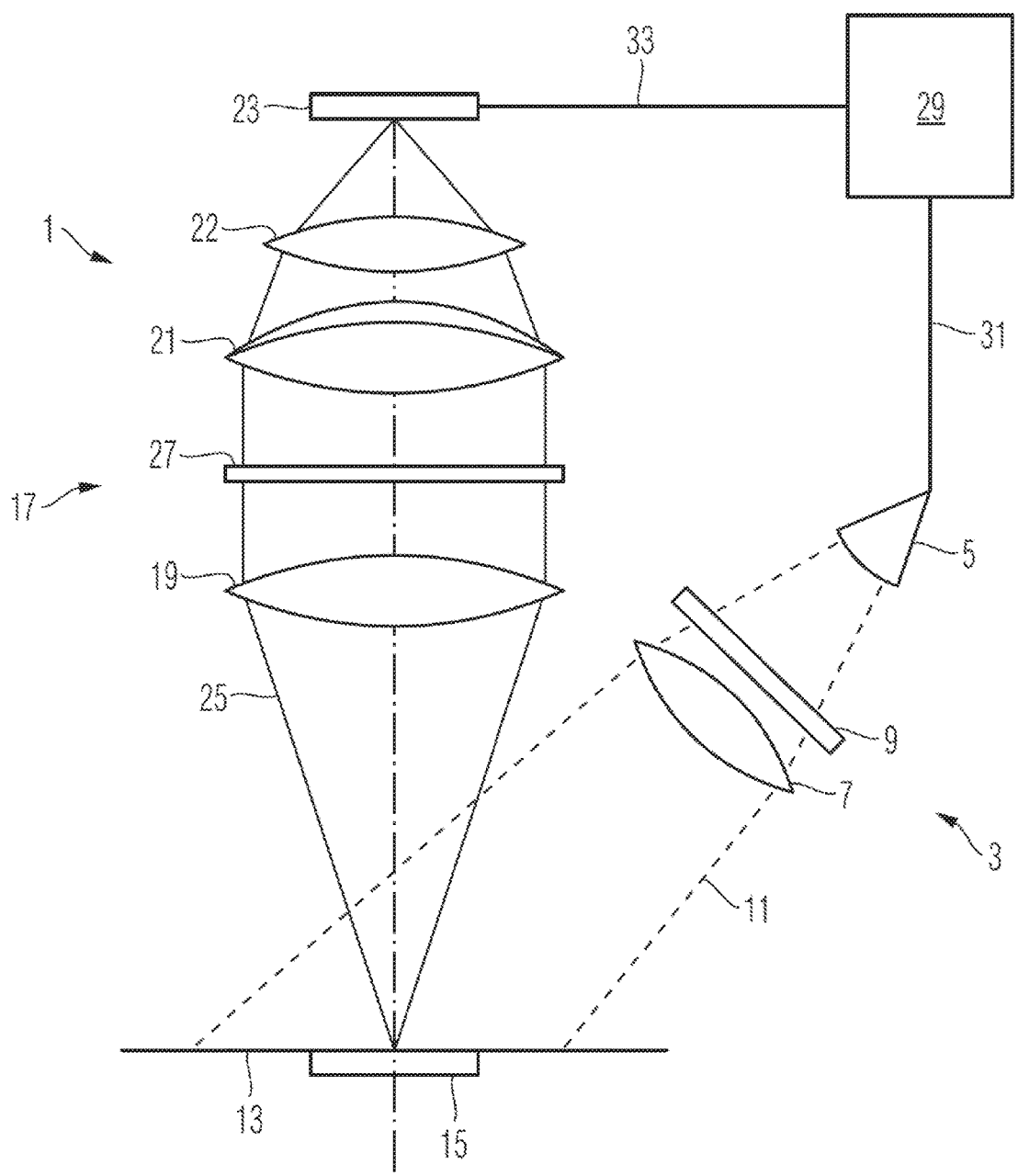
FIG. 1 shows an exemplary embodiment of a fluorescence observation system.

FIG. 1 shows an exemplary embodiment of a fluorescence observation system 1. The fluorescence observation system 1 comprises a light production system 3 comprising at least one light source 5 and one illumination optical unit 7. The at least one light source 5 may comprise a plurality of different light sources, which can each produce excitation light and/or illumination light.

An illumination filter 9, which may be the illumination filter of an optical filter system, is arranged in a beam path 11 between the light production system 3 and an object region 13. As shown in FIG. 1, the illumination filter may also be arranged within the light production system 3.

An object 15, which may contain one or more fluorescent dyes, in particular PpIX, fluorescein, and/or indocyanine green, can be arranged in the object region 13. The light production system 3 is configured to direct excitation light onto the object region 13 for the purposes of exciting fluorescence. Further, the light production system 3 is configured to produce illumination light and direct the latter onto the object region 13. The excitation light and the illumination light may be overlaid in space but at least partly differ from one another in terms of spectral composition. In preferred embodiments, the excitation light and the illumination light are produced by respectively different light sources, the emission intensity of which are individually adjustable in each case.

The excitation light excites a fluorescent dye in the object 15, as a result of which fluorescence light is omitted. Further, the illumination light incident on the object 15 is at least partly reflected by the latter. The illumination light reflected by the object 15 and the fluorescence light emitted by the object 15 are detected by a detection system 17. By way of example, the detection system 17 may comprise a lens 19, a zoom system consisting of the lens elements 21 and 22, and a spatially resolving camera 23. A detection filter 27, which may be a detection filter of an optical filter system, is arranged in a beam path 25 between the object region 13 and the camera 23.

The fluorescence observation system may further comprise a controller 29 which is connected, firstly, to the light production system 3 via a connection 31 and, secondly, to the camera 23 via a connection 33. The controller 29 can control the light production system 3 via the connection 31. By way of example, the controller 29 may control the emission intensity of the at least one light source 5 or control the individual light sources 5 or switch these on and off. If a plurality of illumination filters 9 are provided in a filter changer, in particular a filter wheel, the controller 29 can select the illumination filter to be inserted into the beam path 11 and can cause said illumination filter to be introduced into the beam path 11.

The controller 29 receives the images detected by the camera 23 via the connection 33. The controller 29 can process the received images and prompt the presentation thereof on a display appliance. By way of example, a screen or other image-presenting appliances may be considered as a display appliance.

The modes of operation of the fluorescence observation system may be implemented by the controller 29.

Figure 2A:
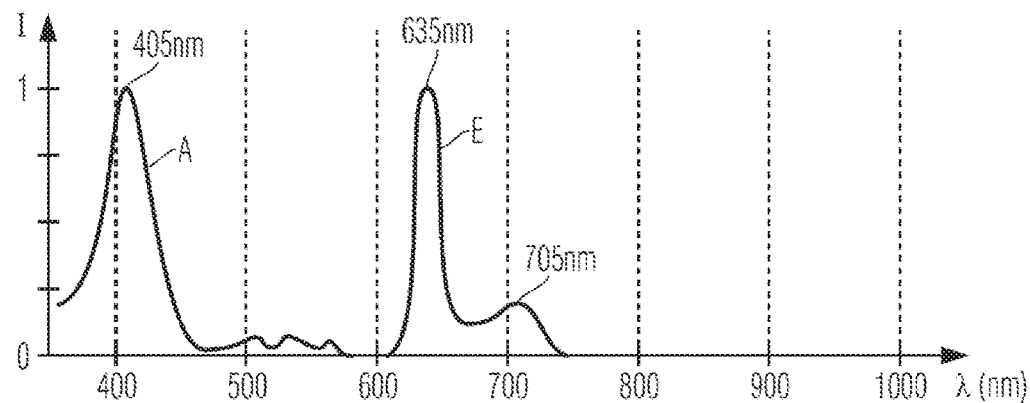
FIG. 2A shows the normalized absorption spectrum and emission spectrum of PpIX.
Figure 2B:
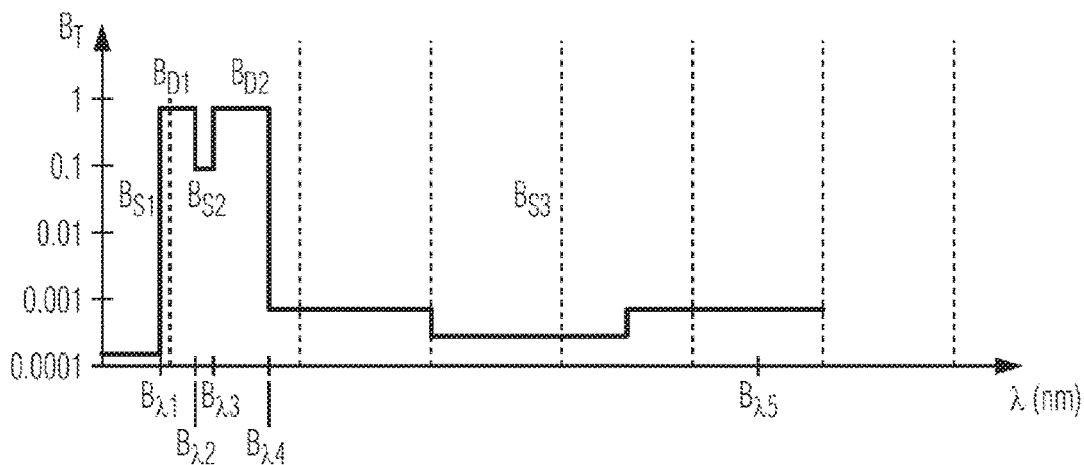
FIG. 2B shows an exemplary transmission spectrum of an illumination filter.
Figure 2C:
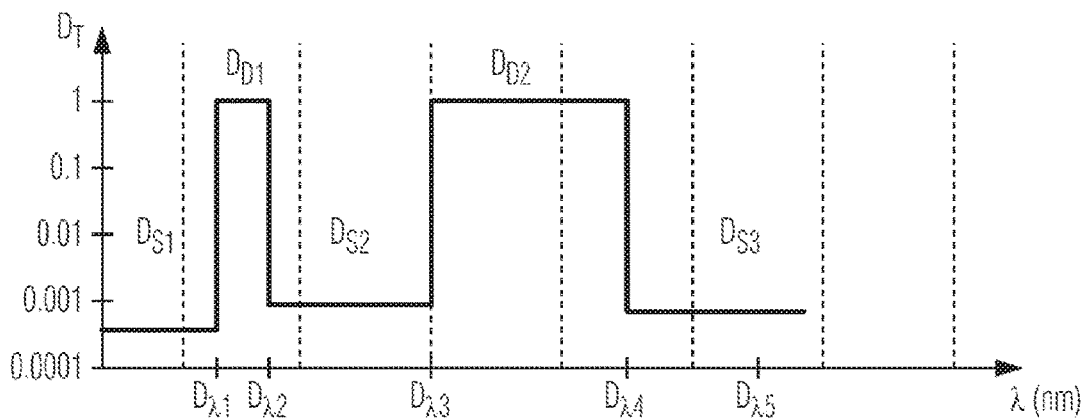
FIG. 2C shows an exemplary transmission spectrum of a detection filter which is matched to the illumination filter shown in FIG. 2B.

FIGS. 2A, 2B, and 2C are used to explain an exemplary embodiment of an optical filter system suitable for detecting PpIX. FIG. 2A shows the absorption spectrum (A) and the emission spectrum (E) of the fluorescent dye PpIX. As explained above, the absorption spectrum (A) of the fluorescent dye PpIX has a maximum at approximately 405 nm. The emission spectrum (E) has a main maximum at approximately 635 nm and a secondary maximum at approximately 705 nm.

FIGS. 2B and 2C each show a transmission spectrum of an illumination filter and of a detection filter, respectively, which together form an optical filter system and together are suitable for exciting PpIX and detecting the fluorescence light thereof. The transmission spectra of the illumination filter and of the detection filter are each embodied in such a way that the image impression to which the surgeon is accustomed from conventional analog fluorescence microscopes for objects stained with the fluorescent dye PpIX is reproduced. This image impression comprises a blue overview image which provides the surgeon with an overview of the object and the emission of PpIX in the range from approximately 600 nm to 750 nm. Consequently, the surgeon is provided with a blue overview image having regions fluorescing in red.

By way of example, a laser with a central emission wavelength Λ1 of 405 nm or a violet LED, the central emission wavelength Λ2 of which lies at approximately 410 nm, may be used to excite the fluorescent dye.

A blue LED, which has a central emission wavelength of 450 nm, may be used to provide the illumination light.

The transmission spectrum TB of the illumination filter, in a wavelength range from 350 nm to 1000 nm, has a first stopband $^B$S1 from 350 nm to $^B\lambda1$ with a mean transmittance of $^B$TS1, a first passband $^B$D1 from $^B\lambda1$ to $^B\lambda2$ with a mean transmittance of $^B$TD1, a second stopband $^B$S2 from $^B\lambda2$ to $^B\lambda3$ with a mean transmittance of $^B$TS2, a second passband $^B$D2 from $^B\lambda3$ to $^B\lambda4$ with a mean transmittance of $^B$TD2, and a third stopband $^B$S3 from $^B\lambda4$ to $^B\lambda5$ with a mean transmittance of $^B$TS3. Here:

350 nm$\leq$$^B\lambda1$<$^B\lambda2$<$^B\lambda3$<$^B\lambda4$<$^B\lambda5$$\leq$1000 nm.

Moreover, the mean transmittances $^B$TD1 and $^B$TD2 of the passbands $^B$D1 and $^B$D2 are in each case greater than the transmittances of the stopbands surrounding the passbands, i.e., $^B$TS1<$^B$TD1; $^B$TD1>$^B$TS2; $^B$TS2<$^B$TD2 and $^B$TD2>$^B$TS3. The illumination filters explained below, which are shown in FIGS. 3B, 4B, 5B and 6B, likewise have this basic structure.

The first stopband BS1 of the illumination filter extends from 350 nm to $^B\lambda1$=390 nm and serves to suppress ultraviolet light and thereby protect the exposed object from unnecessary impingement with intensity. Moreover, the first stopband $^B$S1 delimits the spectral range of the excitation light such that only those spectral ranges of the excitation light in which the absorption spectrum (A) of the fluorescent dye has a high absorption value, for example $I_A$>0.5, are incident on the object.

The first passband $^B$D1 of the illumination filter is dimensioned, i.e., the wavelengths $^B\lambda1$ and $^B\lambda2$ are selected, such that excitation light can be directed onto the object region. In particular, the first passband $^B$D1 is selected such that the spectral range from $^B\lambda1$ to $^B\lambda2$ contains, or is restricted to, that spectral range of the absorption spectrum (A) of PpIX, for which the following applies: $I_A$>0.5. This means that the first passband $^B$D1 contains the spectral range in which the absorption spectrum (A) of PpIX has a high intensity value $I_A$. In the present example, the following applies: $^B\lambda$=415 nm.

The second passband $^B$D2 of the illumination filter is dimensioned, i.e., the wavelengths $^B\lambda3$ and $^B\lambda4$ are selected, such that illumination light in the blue spectral range can be transmitted to the object region. By way of example, the second passband $^B$D2 may be centered around a central emission wavelength of the blue LED and may include, or be restricted to, the spectral range of the emission spectrum of the blue LED in which the emission intensity is greater than a predetermined value, for example 0.5. In the present example, the following applies: $^B\lambda3$=430 nm and $^B\lambda4$=470 nm.

The second stopband $^B$S2, delimited by the wavelengths $^B\lambda2$ and $^B\lambda3$, lies between the first passband $^B$D1 and the second passband $^B$D2. The second stopband $^B$S2 serves to spectrally separate excitation light, which is transmitted through the first passband $^B$D1, and illumination light, which is transmitted through the second passband $^B$D2. This can prevent illumination light from contributing to the excitation of the fluorescent dye and excitation light from contributing to the illumination of the object region. This is advantageous, in particular, if use is made of individually controllable light sources, one of which produces the excitation light and the other one of which produces the illumination light, and the intensities of the excitation light and of the illumination light are adjusted according to certain criteria.

The illumination filter has the third stopband $^B$S3 for suppressing the excitation of the fluorescent dye by light having a wavelength of more than $^B\lambda4$ (470 nm). Particularly in the emission range of the fluorescent dye, i.e., in the spectral range in which the fluorescent dye has a significant emission intensity, for example $I_E$>0.1, said stopband has a particularly low mean transmittance. In the present example, a range from 600 nm to 750 nm of the third stopband $^B$S3 has a mean transmittance of approximately 0.0005. This stops the emission range of the fluorescent dye being swamped by illumination light and/or excitation light.

The wavelengths $^B\lambda1$ and $^B\lambda2$, which define the spectral range of the first passband $^B$D1 of the illumination filter, may be selected depending on the light sources for producing the excitation light that are used in the light production system of the fluorescence observation system. By way of example, if a laser with the central emission wavelength Λ1 of 405 nm is used for exciting the fluorescent dye, the first passband $^B$D1 may cover a correspondingly small spectral range; in particular, it is possible to select $^B\lambda1$>400 nm and $^B\lambda2\leq$410 nm. If, instead, a violet LED with a central emission wavelength Λ2 of 410 nm is selected, the first passband $^B$D1 may be slightly broader, for example $^B\lambda1\leq$380 nm and $^B\lambda2$>420 nm. The second passband may also be selected depending on the light source that is used to produce the illumination light.

The transmission spectrum, shown in FIG. 2C, of the detection filter, in the wavelength range from 350 nm to 1000 nm, has a first stopband $^D$S1 from 350 nm to $^D\lambda1$ with a mean transmittance of $^D$TS1, a first passband $^D$D1 from $^D\lambda1$ to $^D\lambda2$ with a mean transmittance of $^D$TD1, a second stopband $^D$S2 from $^{D2}$ to $^D\lambda3$ with a mean transmittance of $^D$TS2, a second passband $^D$D2 from $^D\lambda3$ to $^D\lambda4$ with a mean transmittance of $^D$TD2, and a third stopband $^D$S3 from $^D\lambda4$ to $^D\lambda5$ with a mean transmittance of $^D$TS3. Here: 350 nm$\leq$$^D\lambda1$<$^D\lambda2$<$^D\lambda3$<$^D\lambda4$<$^D\lambda5\leq$1000 nm.

Moreover, the mean transmittances of the passbands are respectively greater than the mean transmittances of the stopbands delimiting the respective passbands, i.e., $^D$TS1<$^D$TD1; $^D$TD1>$^D$TS2; $^D$TS2<$^D$TD2 and $^D$TD2>$^D$TS3. This general structure of the transmission spectrum of the detection filter equally applies to the transmission spectra of further detection filters shown in FIGS. 3C, 4C, and 5C.

The first stopband of the detection filter $^D$S1 is configured, i.e., the wavelength $^D\lambda1$ is selected, such that the first stopband $^D$S1 includes the first passband $^B$D1 of the illumination filter. Further, the first stopband $^D$S1 of the transmission filter may include the first stopband $^B$S1 and/or second stopband $^D$S2 of the illumination filter. As a result, the light which is transmitted through the first passband $^B$D1 of the illumination filter to excite the fluorescent dye is suppressed by the first stopband $^D$S1 of the detection filter. What this achieves is that the color impression of the overview image is not falsified by light in the spectral range, e.g., excitation light, of the first stopband $^D S1$.

The first passband $^D D1$ of the detection filter may be configured, i.e., the wavelengths $^D\lambda 1$ and $^D\lambda 2$ may be selected, such that the first passband $^D D1$ at least partly, typically completely, includes the second passband $^B D2$ of the illumination filter. In particular, the first passband $^D D1$ of the detection filter and the second passband $^B D2$ of the illumination filter may cover the same spectral range, i.e., $^D\lambda 1 = {}^B\lambda 3$ and $^D\lambda 2 = {}^B\lambda 4$. In the present example, the following applies: $^D\lambda 1 = 430$ nm, $^D\lambda 2 = 470$ nm. Further, the detection filter has a second passband $^B D2$, which is configured, i.e., the wavelengths $^D\lambda 3$ and $^D\lambda 4$ are selected, such that emission light of the fluorescent dye PpIX is transmitted well. The second passband $^B D2$ of the detection filter should therefore include the wavelength range from 600 nm to 750 nm. In the present example, the following applies: $^D\lambda 3 = 600$ nm and $^D\lambda 4 = 750$ nm.

The second stopband $^D S2$ of the detection filter, delimited by the wavelengths $^D\lambda 2$ and $^B\lambda 3$, lies between the first passband $^D D1$ of the detection filter and the second passband $^D D2$ of the detection filter. The second stopband $^D S2$ serves firstly to delimit the wavelength range for light for producing the overview image and secondly to suppress ambient light, as a result of which the emission light emitted by the fluorescent dye, which usually has a low intensity, can be detected better.

Further, the detection filter has the third stopband $^D S3$, which likewise serves to suppress ambient light and, as a result thereof, improve the detection of light emitted by the fluorescent dye.

If a laser with the central emission wavelength $\Lambda 1 = 405$ nm is used as a light source for exciting the fluorescent dye PpIX, the first stopband $^D S1$ of the detection filter may be realized by a notch filter or a long-pass filter, which only effectively transmits (e.g., T>0.8) light with a wavelength of more than 440 nm.

In order to suppress ambient light, in particular in the infrared range, which, for example, arises from the room illumination of the room in which the fluorescence observation system is arranged, the wavelength $^D\lambda 4$ of the detection filter may have a lower value. By way of example, the following may apply: $^D\lambda 4 \leq 720$ nm or $^D\lambda 4 \leq 680$ nm.

As a result of the lack of intersection between the emission range of the fluorescent dye and the spectral range used to produce the blue overview image, the excitation light, which is transmitted through the first passband $^B D1$ of the illumination filter, and the illumination light may be directed onto the object region at the same time. As a result of the second stopband $^B S2$ of the illumination filter, the light sources which produce the illumination light and the excitation light may spectrally overlap in this range without falsifying the sought-after image impression. The ratio of the intensities of the excitation light and illumination light may be controlled by controllable light sources; this is advantageous, particularly in the case of weak fluorescence. It is therefore not necessary to directly regulate the intensity of the excitation light and the intensity of the illumination light by the illumination filter, and so the passbands ($^B D1$ and $^B D2$) corresponding thereto may have high transmittances.

Figure 3A:
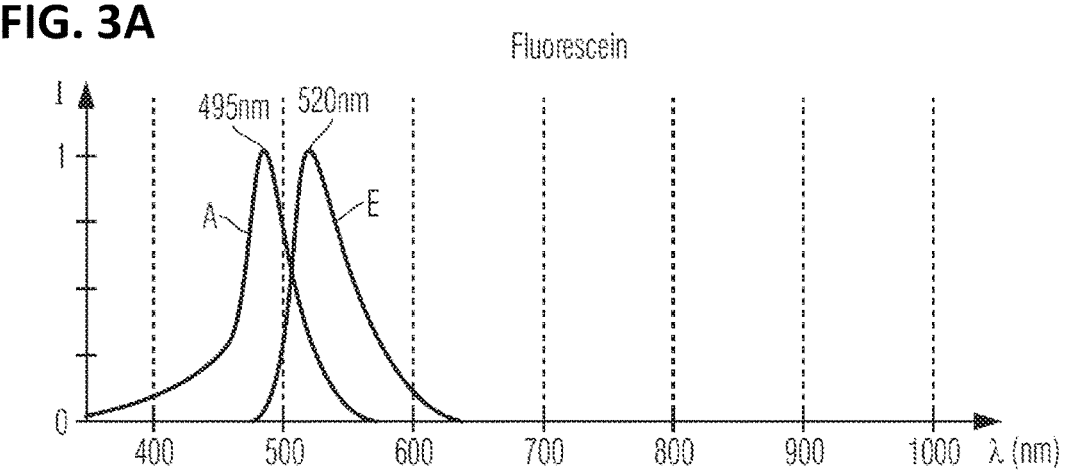
FIG. 3A shows the normalized absorption spectrum and emission spectrum of fluorescein.
Figure 3B:
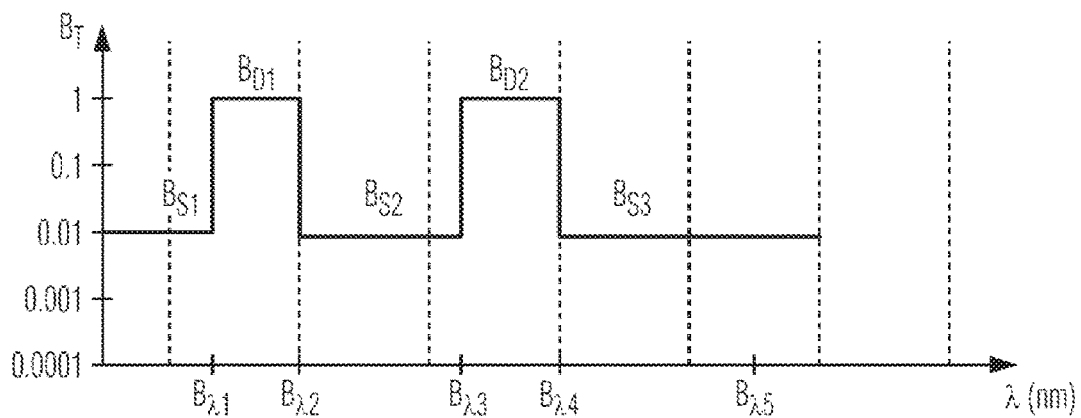
FIG. 3B shows an exemplary transmission spectrum of an illumination filter.
Figure 3C:
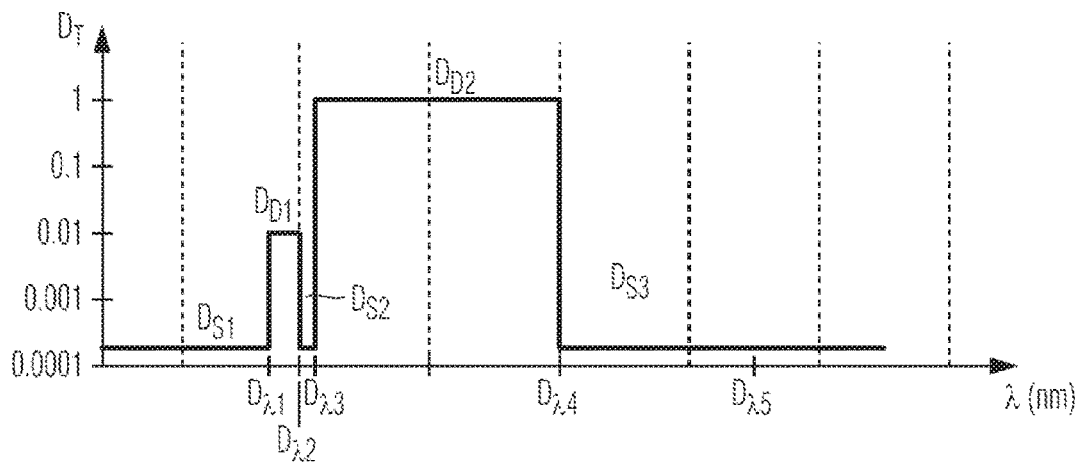
FIG. 3C shows an exemplary transmission spectrum of a detection filter which is matched to the illumination filter shown in FIG. 3B.

FIGS. 3A, 3B, and 3C are used to explain an exemplary embodiment of an optical filter system suitable for detecting fluorescein. FIG. 3A shows the absorption spectrum A and the emission spectrum E of the fluorescent dye fluorescein. As explained above, the absorption spectrum has a maximum at approximately 495 nm. The maximum of the emission spectrum lies at approximately 520 nm.

A whitish overview image and the emission of fluorescein from approximately 500 nm to 650 nm should be provided for the fluorescent dye fluorescein, to which the surgeon is accustomed from conventional analog microscopy systems.

By way of example, a laser with a central emission wavelength $\Lambda 3$ of approximately 488 nm or a cyan LED having a central emission wavelength $\Lambda 4$ of approximately 490 nm may be used to excite fluorescein. In order to produce the whitish overview image, i.e., to produce the illumination light, the light source for producing the excitation light may be used in conjunction with an additional red LED with a central emission wavelength of approximately 660 nm. Moreover, or alternatively, the cyan LED and/or a blue LED may be used together with the red LED for producing the illumination light.

FIGS. 3B and 3C show transmission spectra of an illumination filter and of a detection filter, respectively, of an optical filter system. The first passband $^B D1$ of the illumination filter is configured, i.e., the wavelengths $^B\lambda 1$ and $^B\lambda 2$ are selected, such that both excitation light for exciting the fluorescence of fluorescein and bluish illumination light can be transmitted. Therefore, the first passband $^B D1$ of the illumination filter should comprise a spectral range in which fluorescein has a high absorption and a low emission intensity. This can prevent the excitation light from swamping the emission light emitted by the object. In the present example, the following applies: $^B\lambda 1 = 430$ nm, $^B\lambda 2 = 500$ nm.

The second passband $^B D2$ of the illumination filter is selected, i.e., the wavelengths $^B\lambda 3$ and $^B\lambda 4$ are selected, such that illumination light in the red wavelength range, in particular the illumination light produced by the red LED, can be transmitted well.

The second stopband $^B S2$ of the illumination filter should include the spectral range in which fluorescein has a high value of emission intensity. This prevents excitation light and/or illumination light and/or ambient light swamping the fluorescence light.

The first stopband $^B S1$ and the third stopband $^B S3$ of the illumination filter serve to suppress ambient light and protect the object region from an unnecessary exposure to excitation light, illumination light, and ambient light.

The first passband $^D D1$ of the detection filter (see FIG. 3C) serves to transmit, with a greatly reduced intensity, a blue spectral range of the illumination light, which may coincide with the excitation light. The mean transmittance $^D TD1$ of the first passband $^D D1$ may be, for example, 0.01 and it is selected such that a whitish color impression for the overview image is produced in combination with the illumination light transmitted through the second passband $^D D2$. In the present example, the following applies: $^D\lambda 1 = 480$ nm, $^D\lambda 2 = 500$ nm. If a laser with a central emission wavelength $\Lambda 3$ of 488 nm is used to excite fluorescein, $^D\lambda 1$ should be selected to be greater than or equal to 490 nm. For the illumination in the blue spectral range, use can be made of, for example, a cyan LED. In this case, the first stopband $^D S1$ of the detection filter should have a very low mean transmittance, for example a value that is less than 0.0001.

The second passband $^D D2$ of the detection filter is configured, i.e., the wavelengths $^D\lambda 3$ and $^D\lambda 4$ are selected, such that emission light of the fluorescent dye and also reflected illumination light can be transmitted well in the red spectral range. In the present example, the following applies: $^D\lambda 3 = 510$ nm, $^D\lambda 4 = 700$ nm.

The second stopband $^D S2$ of the detection filter serves to separate the first passband $^D D1$ and second passband $^D D2$ from one another by way of a low transmittance. Consequently, it is possible to prevent excitation light in the blue spectral range from being transmitted at a higher intensity than what is required for the combination yielding the whitish overview image.

In addition to suppressing ambient light, the first stopband $^{D}S1$ of the detection filter is further configured to strongly suppress some of the excitation light in order thereby to prevent a falsification of the overview image. Further, the third stopband $^{D}S3$ of the detection filter serves to suppress ambient light and thereby protect the object region from excess light exposure.

Since the emission range of fluorescein and the illumination light transmitted through the detection filter are spectrally separated from one another by the optical filter system, the excitation light and the illumination light may be directed onto the object region at the same time. It is possible to produce a whitish overview image by adjusting the intensities of the illumination light in the blue spectral range and red spectral range. This is even the case if the excitation light is part of the illumination light in the blue spectral range, i.e., if, for example, a cyan LED is used for excitation and illumination purposes.

Figure 4A:
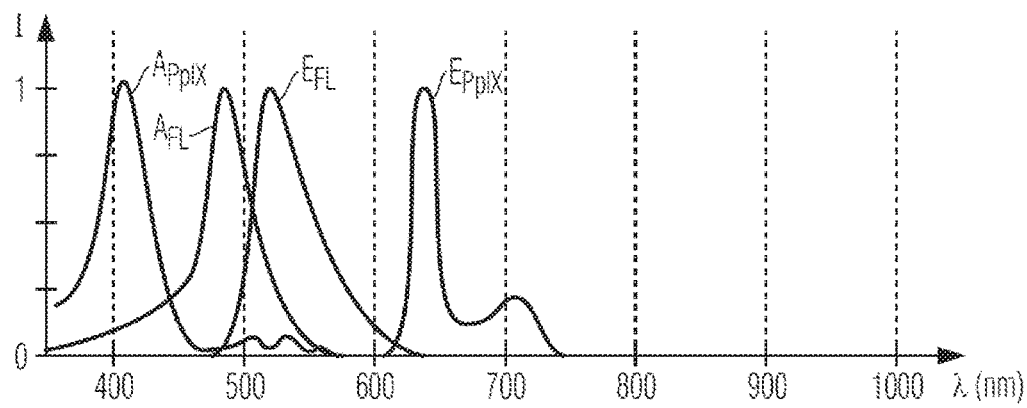
FIG. 4A shows the normalized absorption spectrum and emission spectrum of PpIX and fluorescein.
Figure 4B:
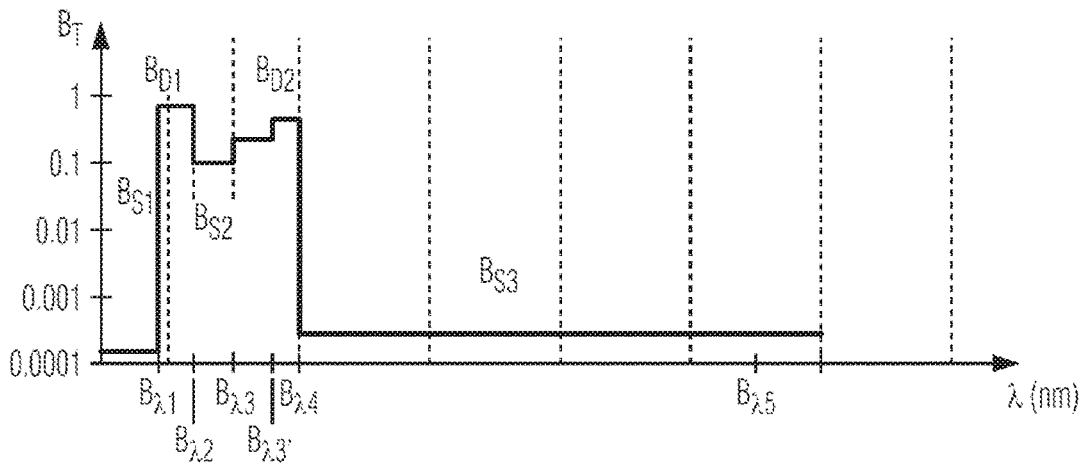
FIG. 4B shows an exemplary transmission spectrum of an illumination filter.
Figure 4C:
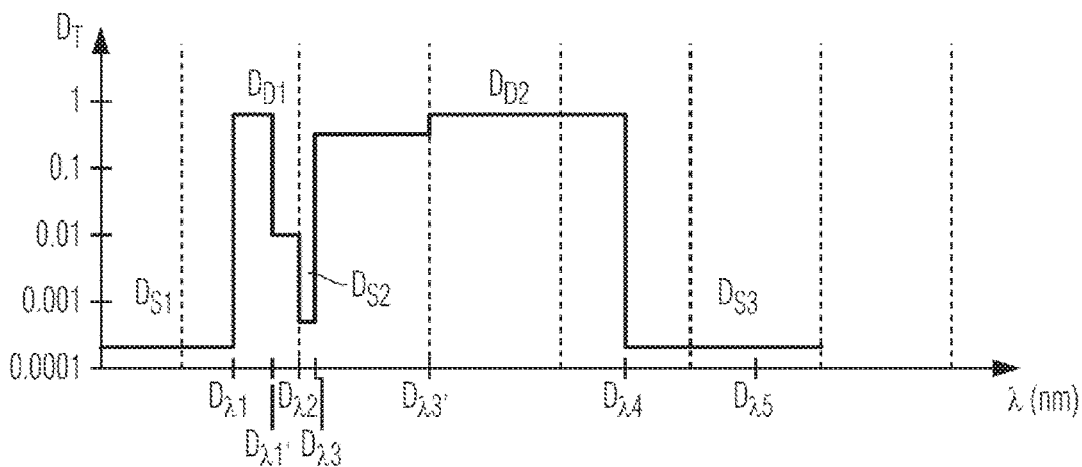
FIG. 4C shows an exemplary transmission spectrum of a detection filter which is matched to the illumination filter shown in FIG. 4B.

An optical filter system which allows simultaneous detection of fluorescence light from PpIX and fluorescein is explained using FIGS. 4A, 4B, and 4C. FIG. 4A shows both the absorption and emission spectra of PpIX ($A_{PpIX}$ and $E_{PpIX}$, respectively) and the absorption and emission spectra of fluorescein ($A_{FL}$ and $E_{FL}$, respectively), which have already been explained above.

The filter system described using FIGS. 4B and 4C is configured to provide a bluish overview image in addition to the emission of the fluorescent dyes PpIX and fluorescein. As before, a laser with a central emission wavelength Λ1 of 405 nm or a violet LED with a central emission wavelength Λ2 of 410 nm may be used to excite PpIX. Likewise, a laser with a central emission wavelength Λ3 of 488 nm or a cyan LED with a central emission wavelength Λ4 of approximately 490 nm may be used to excite fluorescein. Since the absorption spectra of PpIX and fluorescein overlap spectrally, it is possible to use a single laser or a single light source with a central emission wavelength in the overlapping region to simultaneously excite both PpIX and fluorescein. By selecting the central emission wavelength, it is further possible to adjust the ratio of the intensity provided for exciting PpIX and the intensity provided for exciting fluorescein. Alternatively, two or more light sources may be used to excite the two fluorescent dyes, with the emission ranges of the light sources typically not overlapping such that each fluorescent dye can be excited with an individually adjustable intensity.

FIG. 4B shows the transmission spectrum of the illumination filter. The first passband $^{B}D1$ of the illumination filter is configured, i.e., the wavelengths $^{B}λ1$ and $^{B}λ2$ are selected, such that the first passband $^{B}D1$ of the illumination filter includes the spectral range in which the absorption spectrum of PpIX has high values (e.g., $I_{A,PpIX}>0.5$). Therefore, the first passband $^{B}D1$ of the illumination filter is configured to transmit excitation light for exciting PpIX. In the present example, $^{B}λ1=390$ nm, $^{B}λ2=415$ nm. The second passband $^{B}D2$ of the illumination filter is configured to transmit excitation light for exciting fluorescein and, to this end, includes at least part of the spectral range in which the absorption spectrum of fluorescein has high values. Further, the second passband $^{B}D2$ of the illumination filter serves to transmit illumination light for producing the overview image. In order to be able to ensure this dual function, provision may be made for the second passband $^{B}D2$ of the illumination filter to have two different ranges, in which different mean transmittances may be provided in each case. In particular, a range from $^{B}λ3$ to $^{B}λ3'$ may have a first mean transmittance $^{B}W1$ and a range from $^{B}λ3'$ to $^{B}λ4$ may have a mean transmittance $^{B}W2$, where $^{B}W2$ may be greater than $^{B}W1$. In the present example, the following applies: $^{B}λ3=450$ nm, $^{B}λ3'=480$ nm and $^{B}λ4=500$ nm.

The second stopband $^{B}S2$ of the illumination filter serves to suppress crosstalk between the excitation light for exciting the PpIX fluorescence and the excitation light for exciting the fluorescein fluorescence. As a result of this, the two fluorescent dyes may be excited precisely and independently of one another. The first stopband $^{B}S1$ and the third stopband $^{B}S3$ of the illumination filter serve to suppress ambient light. Further, the third stopband $^{B}S3$ of the illumination filter serves the purpose of directing no excitation and illumination light onto the object region in the spectral range of the emission of the two fluorescent dyes. As a result, the fluorescence can be detected better.

FIG. 4C shows the transmission spectrum of the detection filter. The first stopband $^{D}S1$ of the detection filter is configured, i.e., the wavelengths $^{D}λ1$ are selected, such that the first stopband $^{D}S1$ of the detection filter includes the first passband $^{B}D1$ of the illumination filter. As a result of this, the excitation light for exciting PpIX may be suppressed. Further, the first stopband $^{D}S1$ of the detection filter may include the second stopband $^{B}S2$ of the illumination filter. Like in the example shown here, the following may apply: $^{D}λ1=^{B}λ3$ $(=450$ nm).

The second stopband $^{D}S2$ of the detection filter is configured, i.e., the wavelengths $^{D}λ2$ and $^{D}λ3$ are selected, such that excitation light for exciting fluorescein transmitted through the illumination filter may be suppressed. In particular, the spectral range from $^{D}λ2$ to $^{D}λ3$ may include the spectral range of $^{B}λ3'$ to $^{B}λ4$. As a result of this, the excitation light for exciting fluorescein is efficiently suppressed.

The first passband $^{D}D1$ of the detection filter serves to transmit blue illumination light in the spectral range from $^{B}λ3$ to $^{B}λ3'$. Within the first passband $^{L}D1$ of the detection filter, provision may be made of a range from $^{D}λ1$ to $^{D}λ1'$ with a mean transmittance of $^{D}W1$ and a further range from $^{D}λ1'$ to $^{D}λ2$ with a mean transmittance of $^{D}W2$, where, in particular, $^{D}W2<^{D}W1$ applies. If the optical filter system is operated with a broadband light source, where excitation light and illumination light are directed onto the object region after one another sequentially in time, the range from $^{D}λ1'$ to $^{D}λ2$ may be used to correct the color impression of the overview image produced by the broadband illumination. In the present example, the following applies: $^{D}λ1'=480$ nm.

The second passband $^{C}D2$ of the detection filter should include the spectral range of the emission light of PpIX and fluorescein. In the present example, the following applies: $^{D}λ3=510$ nm, $^{D}λ4=750$ nm. Consequently, the fluorescence light produced by the fluorescent dyes may be transmitted through the detection filter and be detected.

The third stopband $^{D}S3$ of the detection filter serves to suppress ambient light, as a result of which the detection of the fluorescence light is improved.

As already explained above, a laser with a central emission wavelength Λ1 of 405 nm or a violet LED with a central emission wavelength Λ2 of approximately 410 nm may be used to excite the fluorescent dye PpIX. Further, a laser with a central emission wavelength Λ3 or a cyan LED with a central emission wavelength Λ4 of approximately 490 nm may be used to excite the fluorescent dye fluorescein. Further, a blue LED with a central emission wavelength of approximately 450 nm may be used to provide a blue overview image. Since the illumination light produced by the blue LED and the emission light of the fluorescent dyes are not spectrally overlaid, the excitation light and the illumination light may be directed onto the object region at the same time.

As an alternative to the blue overview image, which surgeons are accustomed to in conjunction with the fluorescent dye PpIX, it is also possible to provide a whitish overview image, as surgeons are accustomed to in conjunction with the fluorescent dye fluorescein. In this variant, the illumination light transmitted through the passbands and stopbands of the illumination filter serves to produce the overview image. However, since there is spectral overlap between the illumination light and the excitation light in this variant, the excitation light and the illumination light are directed sequentially in time, i.e., in succession, onto the object region and images are respectively detected while the excitation light is directed onto the object region and while the illumination light is directed onto the object region. It may already be sufficient to time-modulate the intensity of either the illumination light or the excitation light in order thereby to correspondingly ascertain the intensity component in the emission range of the fluorescent dyes caused by the illumination light and to correspondingly correct the images.

If, for the purposes of producing the illumination light and producing the excitation light, use is made of a plurality of light sources whose emission intensity is controllable, it is possible, firstly, to match the emission intensities of the different fluorescent dyes to one another. Secondly, it is possible to adjust the intensity of the illumination light to the intensity of the fluorescence light. In particular, it is possible to completely dispense with the illumination light such that only the fluorescence light of the fluorescent dyes in the yellow and red spectral range is detected.

As an alternative to the illumination in the blue spectral range from $^B\lambda 3$ to $^B\lambda 3'$, a passband in the infrared spectral range, in particular in the spectral range from 750 nm to 1000 nm, may be provided in the transmission spectrum of the illumination filter, it being possible to use said passband for illuminating the object region with infrared light. Correspondingly hereto, the transmission spectrum of the detection filter has an extended second passband $^D\!D2$ or a further third passband in the infrared.

Figure 5A:
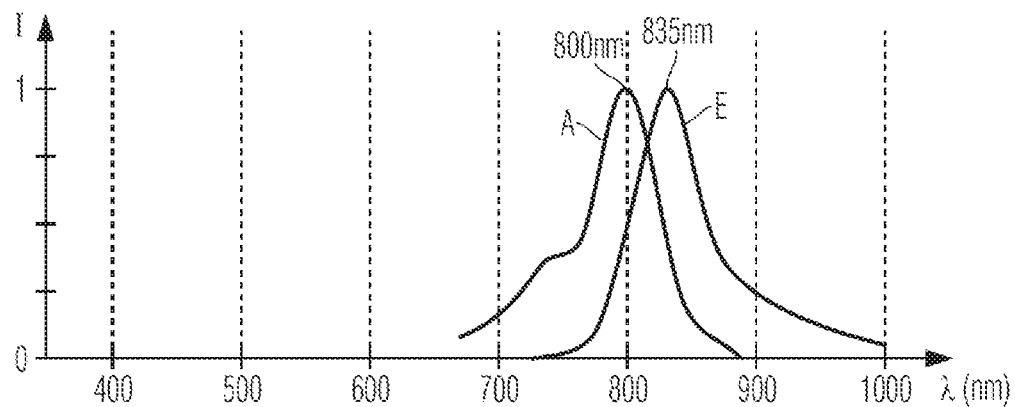
FIG. 5A shows the normalized absorption spectrum and emission spectrum of indocyanine green.
Figure 5B:
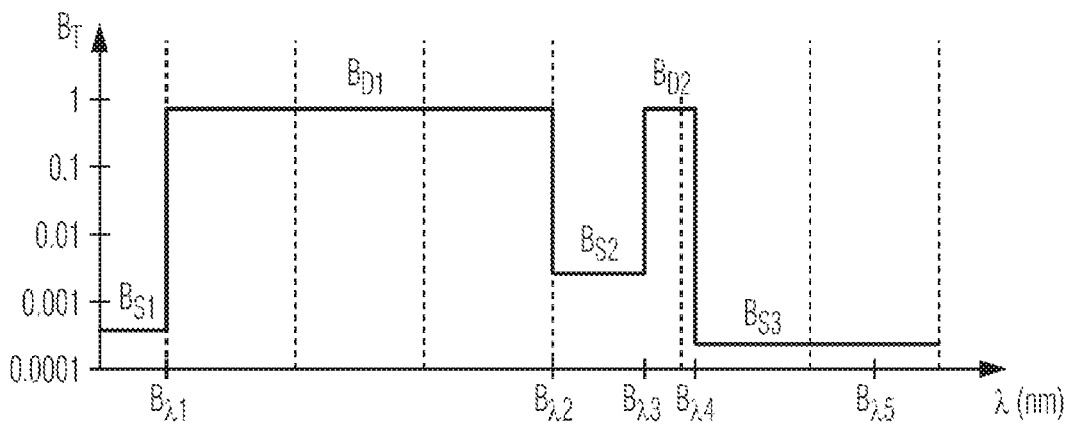
FIG. 5B shows an exemplary transmission spectrum of an illumination filter.
Figure 5C:
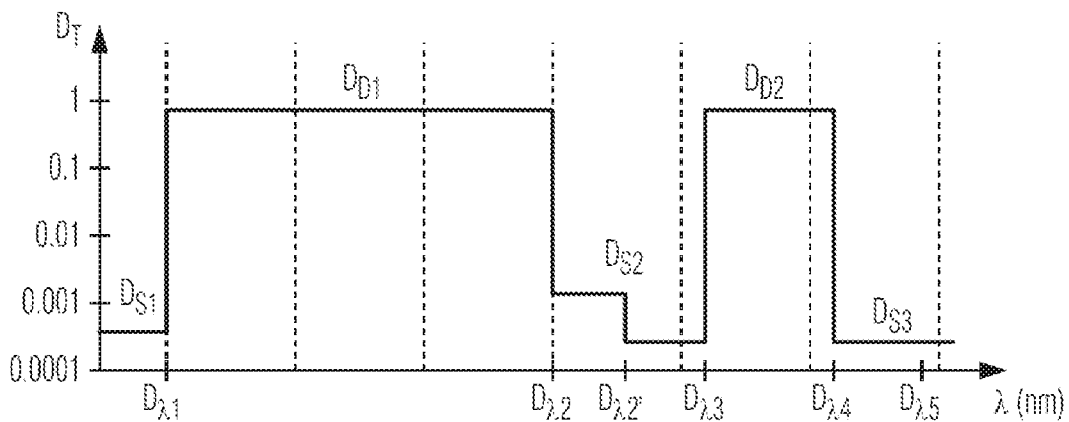
FIG. 5C shows an exemplary transmission spectrum of a detection filter which is matched to the illumination filter shown in FIG. 5B.

An optical filter system which allows detection of fluorescence light from ICG is explained using FIGS. 5A, 5B and 5C. FIG. 5A shows the absorption spectrum A and the emission spectrum E of indocyanine green. As explained previously, the absorption spectrum has a maximum at approximately 800 nm and the emission spectrum has a maximum at approximately 835 nm.

Using the optical filter system explained using FIGS. 5B and 5C, the surgeon should be provided with an overview image from the visible spectral range and the fluorescence of indocyanine green. Since the emission of indocyanine green lies in the infrared spectral range, the fluorescence is indicated by overlaying the fluorescence image onto the overview image, wherein the fluorescence image may be presented, for example, using a false color representation, by contours, shadows, hatching and the like.

By way of example, a laser with a central emission wavelength $\Lambda 5$ of 785 nm or an infrared LED with a central emission wavelength $\Lambda 6$ of approximately 800 nm may be used to excite indocyanine green. A broadband light-emitting diode, for example an RGB light-emitting diode, may be used to provide the illumination light.

FIG. 5B shows the transmission spectrum of the illumination filter. The second passband $^B\!D2$ of the illumination filter is configured, i.e., the wavelengths $^B\lambda 3$ and $^B\lambda 4$ are selected, such that excitation light for exciting indocyanine green can be transmitted through the illumination filter. In the present example, the following applies: $^B\lambda 3$=770 nm and $^B\lambda 4$=810 nm.

The first passband $^B\!D1$ of the illumination filter is configured, i.e., the wavelengths $^B\lambda 1$ and $^B\lambda 2$ are selected, such that illumination light in the visible spectral range can be transmitted through the illumination filter onto the object region. In the present example, the following applies: $^B\lambda 1$=400 nm and $^B\lambda 2$=700 nm. Since both the absorption spectrum and the emission spectrum of indocyanine green substantially do not lie in the visible spectral range, the boundaries of the first passband D1 of the illumination filter may be selected substantially freely between 400 nm and approximately 750 nm within the visible spectral range. The second stopband $^B\!S2$ of the detection filter is provided for delimiting the excitation light from the illumination light. The first stopband $^B\!S1$ and the third stopband $^B\!S3$ serve to suppress disadvantageous spectral ranges. Further, the third spectral range $^B\!S3$ of the illumination filter serves to suppress excitation light which includes the emission range of indocyanine green.

FIG. 5C shows the transmission spectrum of the detection filter. The first passband $^D\!D1$ of the detection filter is configured, i.e., the wavelengths $^D\lambda 1$ and $^D\lambda 2$ are selected, such that the illumination light can be transmitted through the detection filter. In particular, the first passband $^D\!D1$ of the detection filter may, at least partly or else completely, include the first passband $^B\!D1$ of the illumination filter. In particular, as in the illustrated example, the following may apply: $^D\lambda 1$=$^B\lambda 1$ and $^D\lambda 2$=$^B\lambda 2$.

The second passband $^D\!D2$ of the detection filter is configured, i.e., the wavelengths $^D\lambda 3$ and $^D\lambda 4$ are selected, such that emission light of indocyanine green can be transmitted well through the detection filter. In particular, the following applies: $^D\lambda 3$>$^B\lambda 4$, such that the second passband $^D\!D2$ of the detection filter does not spectrally overlap with the second passband $^B\!D2$ of the illumination filter. This prevents the detection of emission light which is overlaid with excitation light. In the present example, the following applies: $^D\lambda 3$=820 nm, $^D\lambda 4$=920 nm.

Accordingly, the second stopband $^D\!S2$ of the detection filter serves to suppress excitation light. In order to suppress the excitation light, use can be made of e.g., a notch filter if use is made of a laser with the central emission wavelength $\Lambda 5$. The second stopband $^D\!S2$ of the detection filter may include a range from $^D\lambda 2$ to $^D\lambda 2'$ with a mean transmittance of at most $^D\!W1$ and a range from $^D\lambda 2'$ to $^D\lambda 3$ with a mean transmittance of at most $^D\!W2$, where $^D\!W2$<$^D\!W1$. In particular, it is possible that $^D\!W2$<0.0001, as a result of which the excitation light is suppressed particularly efficiently.

The first stopband $^D\!S1$ of the detection filter and the third stopband $^D\!S3$ of the detection filter serve to suppress ambient light, as a result of which there is improvement in both the detection of the illumination light for producing the overview image and in the detection of fluorescence light.

Since the illumination light in the visible spectral range between $^B\lambda 1$ and $^B\lambda 2$ does not overlap with the emission light of indocyanine green between $^D\lambda 3$ and $^D\lambda 4$, the excitation light and the illumination light may be directed simultaneously onto the object region.

Figure 6A:
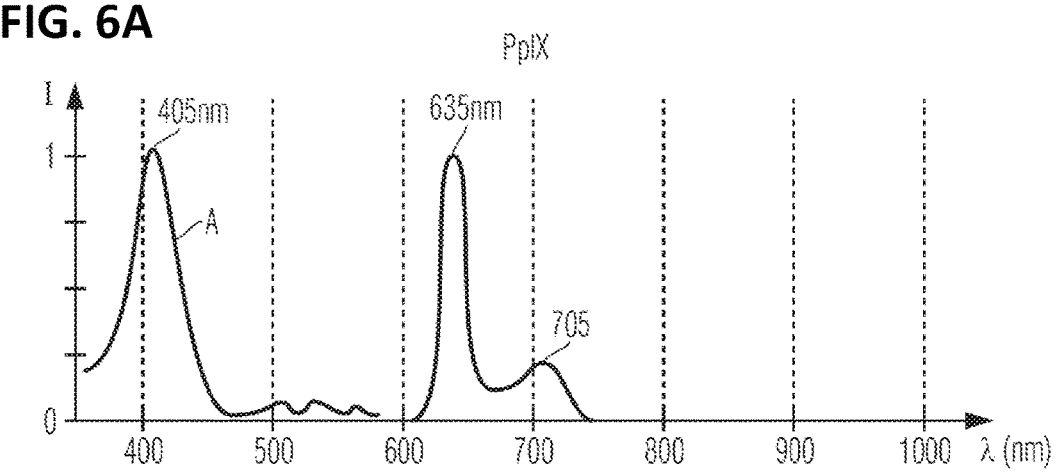
FIG. 6A shows the normalized absorption spectrum and emission spectrum of PpIX.
Figure 6B:
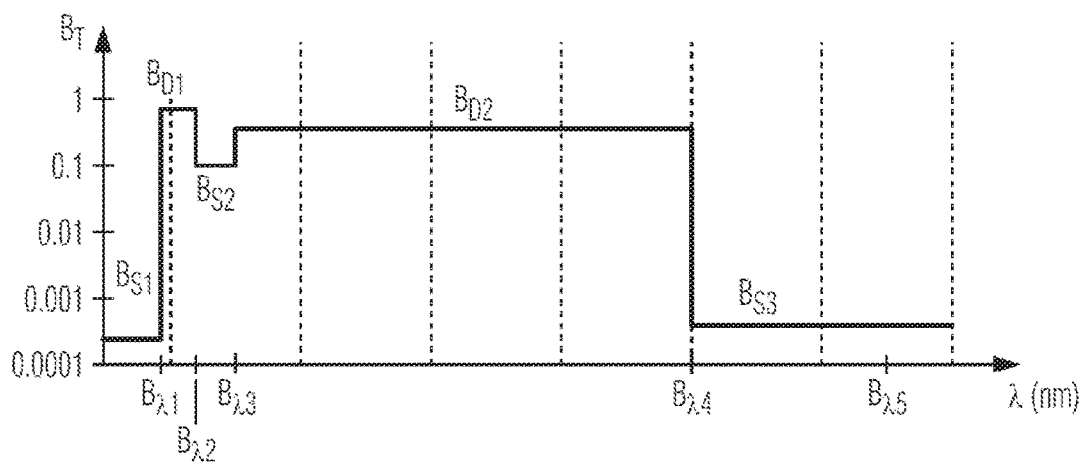
FIG. 6B shows an exemplary transmission spectrum of an illumination filter.
Figure 6C:
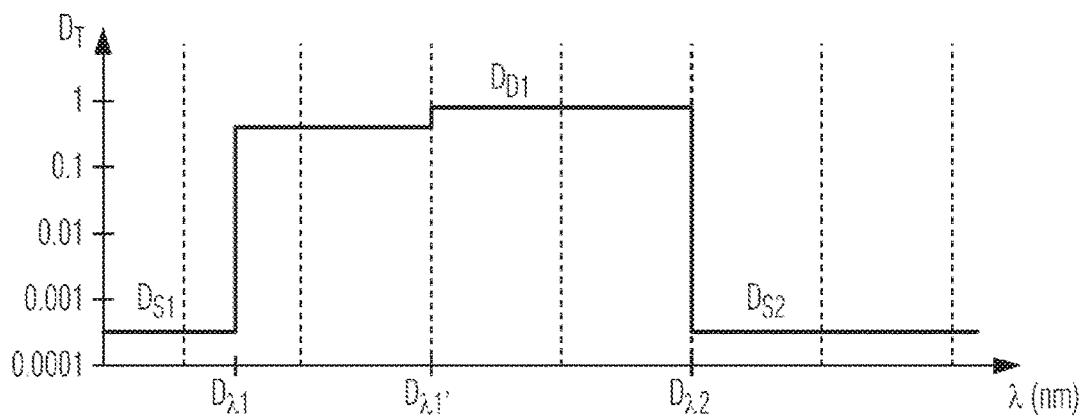
FIG. 6C shows an exemplary transmission spectrum of a detection filter which is matched to the illumination filter shown in FIG. 6B.

FIGS. 6A, 6B, and 6C are used to explain a further optical filter system which can be used with the fluorescent dye PpIX. As already explained above with respect to FIG. 2A, a laser with a central emission wavelength Λ1 of 405 nm or a violet LED with a central emission wavelength Λ2 of approximately 410 nm may be used to excite PpIX. A broadband light-emitting diode, in particular an RGB light-emitting diode, may be used to produce the illumination light in the visible spectral range. Like FIG. 2A, FIG. 6A shows the absorption spectrum and emission spectrum of PpIX.

In contrast to the optical filter system presented in FIGS. 2B and 2C, the filter system presented in FIGS. 6B and 6C should provide an overview image in the visible spectral range and the emission of PpIX. That is to say, instead of the blue overview image provided by the optical filters shown in FIGS. 2B and 2C, an overview image with a high proportion of the visible spectral range and the emission of PpIX therein should be provided to the surgeon.

FIG. 6B shows the transmission spectrum of the illumination filter of the filter system in a wavelength range from 350 nm to 1000 nm. The transmission spectrum of the illumination filter includes a first stopband $^{B}S1$ from 350 nm to $^{B}\lambda 1$ with a mean transmittance of $^{B}TS1$, a first passband $^{B}D1$ from $^{B}\lambda 1$ to $^{B}\lambda 2$ with a mean transmittance of $^{B}TD1$, a second stopband $^{B}S2$ from $^{B}\lambda 2$ to $^{B}\lambda 3$ with a mean transmittance of $^{B}TS2$, a second passband $^{B}D2$ from $^{B}\lambda 3$ to $^{B}\lambda 4$ with a mean transmittance of $^{B}TD2$, and a third stopband $^{B}S3$ from $^{B}\lambda 4$ to $^{B}\lambda 5$ with a mean transmittance of $^{B}TS3$, wherein 350 nm$\leq ^{B}\lambda 1<^{B}\lambda 2<^{B}\lambda 3<^{B}\lambda 4<^{B}\lambda 5\leq$1000 nm. Moreover, the following applies: $^{B}TS1<^{B}TD1$; $^{B}TD1>^{B}TS2$; $^{B}TS2<^{B}TD2$; $^{B}TD2>^{B}TS3$.

The first passband $^{B}D1$ of the illumination filter is configured, i.e., the wavelengths $^{B}\lambda 1$ and $^{B}\lambda 2$ are selected, such that the fluorescent dye PpIX can be excited efficiently. To this end, the first passband $^{B}D1$ includes a spectral range in which the absorption spectrum A of PpIX has high values, for example $I_4>0.5$. In the present example, the following applies: $^{B}\lambda 1$=390 nm and $^{B}\lambda 2$=415 nm.

The second passband $^{B}D2$ of the illumination filter may include a majority of the visible spectral range and may, in this case, include the emission range of PpIX in particular. In the present example, the following applies: $^{B}\lambda 3$=450 nm and $^{B}\lambda 4$=800 nm. As a result of this, the second passband of the illumination filter substantially transmits the visible spectral range above the second stopband $^{B}S2$ of the illumination filter, the latter serving to prevent crosstalk of the excitation light which is transmitted in the first passband $^{B}D1$ into the second passband $^{B}D2$. In the same way, the second stopband $^{B}S2$ serves to prevent crosstalk of the illumination light onto the excitation range of PpIX.

The first stopband $^{B}S1$ and the third stopband $^{B}S3$ of the illumination filter serve to suppress disadvantageous spectral ranges.

FIG. 6C shows the transmission spectrum of the detection filter of the filter system belonging to the illumination filter shown in FIG. 6B. The transmission spectrum of the detection filter has, in the wavelength range from 350 nm to 1000 nm, a first stopband $^{D}S1$ from 350 nm to $^{D}\lambda 1$ with a mean transmittance of $^{D}TS1$, a first passband $^{L}D1$ from $^{D}\lambda 1$ to $^{D}\lambda 2$ with a mean transmittance of $^{D}TD1$ and a second stopband $^{D}S2$ from $^{D}\lambda 2$ to $^{D}\lambda 3$ with a mean transmittance of $^{D}TS2$, wherein the following applies: 350 nm$\leq ^{D}\lambda 1<^{D}\lambda 2<^{D}\lambda 3\leq$1000 nm. Moreover, the following applies: $^{D}TS1<^{D}TD1$; $^{D}TD1>^{D}TS2$.

The first passband $^{D}D1$ of the detection filter is configured, i.e., the wavelengths $^{D}\lambda 1$ and $^{D}\lambda 2$ are selected, such that the illumination light and the emission light can be transmitted through the detection filter. In particular, the first passband $^{D}D1$ of the detection filter includes the second passband $^{B}D2$ of the illumination filter. In particular, $^{D}\lambda 1$ lies between $^{B}\lambda 2$ and $^{B}\lambda 3$ or the following applies: $^{B}\lambda 3$-5 nm$\leq ^{D}\lambda 1\leq ^{B}\lambda 3$+5 nm. As result of this, the first passband $^{D}D1$ of the detection filter substantially starts at the wavelength $^{B}\lambda 3$. Further, the following, in particular, may apply: $^{D}\lambda 2=^{B}\lambda 4$.

The first stopband $^{D}D1$ may include a range from $^{D}\lambda 1$ to $^{D}\lambda 1'$ with a first mean transmittance of at least $^{D}W1$ and a range from $^{D}\lambda 1'$ to $^{D}\lambda 2$ with a mean transmittance of at least $^{D}W2$, where $^{D}W2>^{D}W1$. In this case, the first passband $^{D}D1$ of the detection filter has a particularly high transmittance in the emission range of PpIX, as a result of which the fluorescence can be detected particularly well.

The first stopband $^{D}S1$ and the second stopband $^{D}S2$ of the detection filter serve to suppress ambient light. Further, the first stopband $^{D}S1$ of the detection filter serves to suppress the excitation light.

Since the illumination light and the emission light of PpIX are spectrally overlaid, the illumination light and the excitation light should be directed onto the object region sequentially in time for the purposes of producing the overview image and a fluorescence image. By way of example, if the excitation light is directed onto the object region, it is possible to record a first image which only represents emission light of the fluorescent dye PpIX. A second image is recorded during the illumination of the object region with the illumination light. The first image and the second image can be processed in known ways in order to produce an image which shows both the overview image and fluorescing regions of the object region.

If light sources which have a sufficiently low intensity in the first stopband $^{B}S1$ of the illumination filter and in the third stopband $^{B}S3$ of the illumination filter are used to produce the excitation light and the illumination light, it is also possible to dispense with the illumination filter in the present case. In a further variant of this optical filter system, $^{B}\lambda 4$ is approximately 600 nm. As result of this, the emission range of PpIX is not spectrally overlaid with illumination light, and so a simultaneous illumination of the object region with excitation light and illumination light is also possible.

Figure 7A:
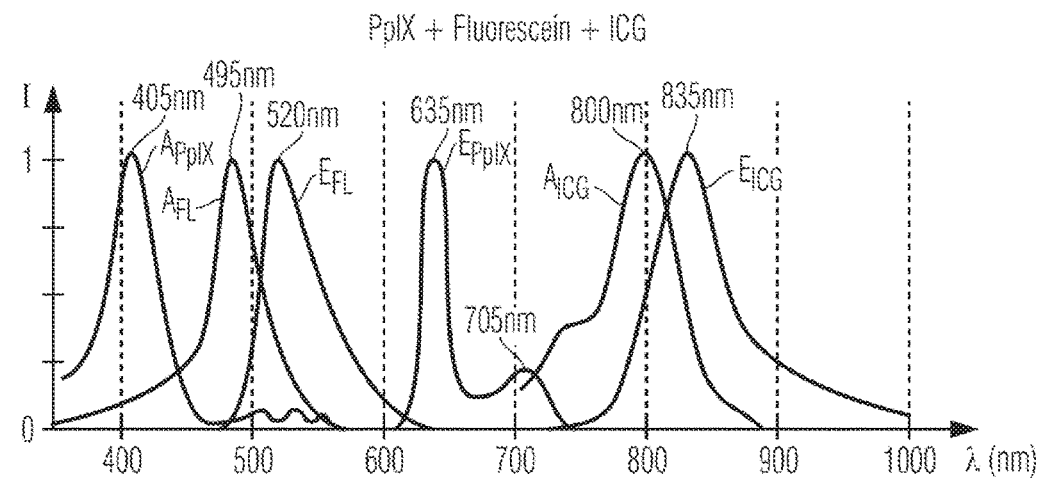
FIG. 7A shows the normalized absorption spectrum and emission spectrum of PpIX, fluorescein, and indocyanine green.
Figure 7B:
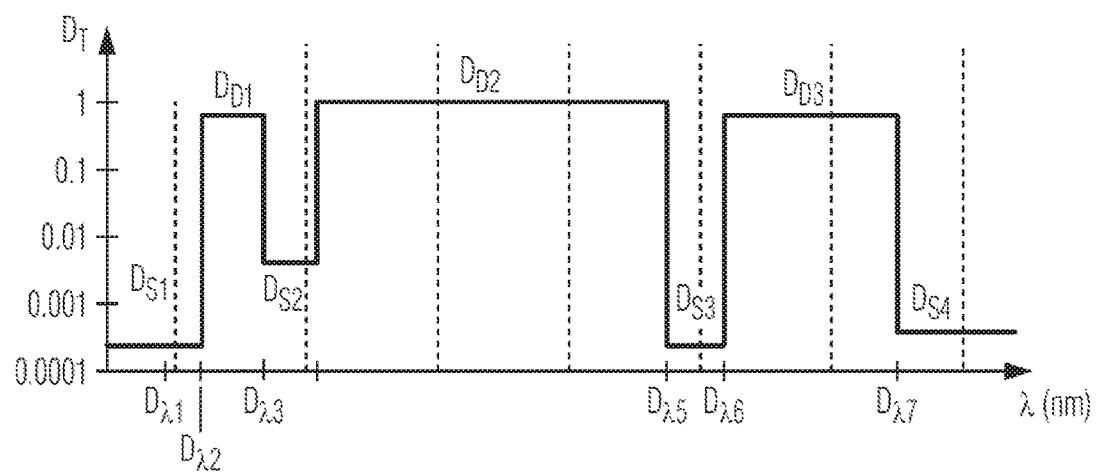
FIG. 7B shows an exemplary transmission spectrum of a detection filter.

FIGS. 7A and 7B are used to explain a detection filter which is used in a fluorescence observation system similar to the fluorescence observation system shown in FIG. 1 but which, in contrast thereto, does not have an illumination filter.

FIG. 7A shows the absorption and emission spectra of the fluorescent dyes PpIX, fluorescein, and ICG, as already explained above.

FIG. 7B shows the transmission spectrum of a detection filter which renders it possible to simultaneously excite all three fluorescent dyes and detect the emission light of the three fluorescent dyes resulting therefrom. Compared to the fluorescence observation system that is illustrated in FIG. 1 and uses the optical filter systems illustrated in FIGS. 2A to 6C, the detection filter need not be changed in order to be able to simultaneously observe the individual fluorescences of the three fluorescent dyes.

The fluorescences of the three fluorescent dyes PpIX, fluorescein, and ICG may be excited using the aforementioned narrowband light sources. In particular, PpIX can be excited by means of a laser with a central emission wavelength Λ1 of 405 nm or a violet LED with a central emission wavelength Λ2 of approximately 410 nm. Further, fluorescein can be excited by means of a laser with a central emission wavelength Λ3 of 488 nm or a cyan LED with a central emission wavelength Λ4 of approximately 490 nm. Finally, indocyanine green can be excited by means of a laser with a central emission wavelength Λ5 of 785 nm or an IR LED with a central emission wavelength Λ6 of approximately 800 nm.

FIG. 7B shows the transmission spectrum of the detection filter, wherein, between 350 nm and 1000 nm, the transmission spectrum has a first stopband $^{D}S1$ from $^{D}\lambda1$ to $^{D}\lambda2$, a first passband $^{L}D1$ from $^{D}\lambda2$ to $^{D}\lambda3$, a second stopband $^{D}S2$ from $^{D}\lambda3$ to $^{D}\lambda4$, a second passband $^{C}D2$ from $^{D}\lambda4$ to $^{D}\lambda5$, a third stopband $^{D}S3$ from $^{D}\lambda5$ to $^{D}\lambda6$ and a third passband $^{D}D3$ from $^{D}\lambda6$ to $^{D}\lambda7$; wherein the stopbands $^{D}S1$, $^{D}S2$, $^{D}S3$ each have a mean transmittance of at most 0.01, typically at most 0.001 or at most 0.0001, and wherein the passbands $^{D}D1$, $^{D}D2$, $^{D}D3$ each have a mean transmittance of at least 0.5, typically at least 0.8 or at least 0.9; and where 350 nm$\leq^{D}\lambda1<^{D}\lambda2<^{D}\lambda3<^{D}\lambda4<^{D}\lambda5<^{D}\lambda6<^{D}\lambda7\leq1000$ nm.

The first stopband $^{D}S1$ of the detection filter is configured, i.e., the wavelengths $^{D}\lambda1$ and $^{D}\lambda2$ are selected, such that the excitation light for exciting PpIX is suppressed. The second stopband $^{D}S2$ of the detection filter is configured, i.e., the wavelengths $^{D}\lambda3$ and $^{D}\lambda4$ are selected, such that the excitation light for exciting fluorescein is suppressed. The third stopband $^{D}S3$ of the detection filter is configured, i.e., the wavelengths $^{D}\lambda5$ and $^{D}\lambda6$ are selected, such that the excitation light for exciting indocyanine green is suppressed. A further fourth stopband $^{D}S4$ of the detection filter may serve to suppress ambient light in the infrared range.

Passbands, in particular the first passband $^{D}D1$, the second passband $^{D}D2$ and the third passband $^{D}D3$, are arranged between the stopbands of the detection filter. The first passband $^{D}D1$ can be used to obtain a blue overview image of the object region. The second passband $^{D}D2$ includes the emission ranges of the fluorescent dyes PpIX and fluorescein. Consequently, emission light of these fluorescent dyes may be transmitted through the second passband $^{D}D2$ of the detection filter and may consequently be detected. The third passband $^{D}D3$ of the detection filter serves to be able to transmit fluorescence light of the fluorescent dye indocyanine green and consequently be able to detect the latter. In particular, as shown in FIG. 7, the following applies: $^{D}\lambda1=390$ nm, $^{D}\lambda2=420$ nm, $^{D}\lambda3=470$ nm, $^{D}\lambda4=505$ nm, $^{D}\lambda5=770$ nm, $^{D}\lambda6=810$ nm and $^{D}\lambda7=920$ nm. If use is made of sufficiently narrowband light sources for the purposes of exciting the fluorescent dyes, it is additionally possible to direct illumination light in a wavelength range from $^{D}\lambda2$ to $^{D}\lambda3$ onto the object region and use the latter to provide an overview image. In this case, it is possible to simultaneously detect both the fluorescence of the three fluorescent dyes and the overview image.

In an alternative exemplary embodiment, a broadband illumination light in the visible spectral range is directed onto the object in place of the illumination light in the spectral range from $^{D}\lambda2$ to $^{D}\lambda3$. However, since the emission ranges of the fluorescent dyes spectrally overlap with the illumination light in this case, the illumination light and the excitation light must be directed onto the object region sequentially in time. Accordingly, images of fluorescence light and images of illumination light are recorded in succession. From the images arising by means of the illumination light and the images arising by means of the fluorescence light, it is possible to produce an image in which it is possible to see both an overview image and the fluorescence of the fluorescent dyes.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An optical filter system for observing fluorescence, comprising:
   an illumination filter; and
   a detection filter;
   wherein a transmission spectrum of the illumination filter, in a wavelength range from 350 nm to 1000 nm, has
      a first stopband ($^{B}S1$) from 350 nm to $^{B}\lambda1$ with a mean transmittance of $^{B}TS1$,
      a first passband ($^{B}D1$) from $^{B}\lambda1$ to $^{B}\lambda2$ with a mean transmittance of $^{B}TD1$,
      a second stopband ($^{B}S2$) from $^{B}\lambda2$ to $^{B}\lambda3$ with a mean transmittance of $^{B}TS2$,
      a second passband ($^{B}D2$) from $^{B}\lambda3$ to $^{B}\lambda4$ with a mean transmittance of $^{B}TD2$, and
      a third stopband ($^{B}S3$) from $^{B}\lambda4$ to $^{BAS}$ with a mean transmittance of $^{B}TS3$;
   wherein 350 nm$\leq^{B}\lambda1<^{B}\lambda2<^{B}\lambda3<^{B}\lambda4<^{B}\lambda5\leq1000$ nm;
   wherein $^{B}TS1<^{B}TD1$; $^{B}TD1>^{B}TS2$; $^{B}TS2<^{B}TD2$; $^{B}TD2>^{B}TS3$;
   wherein a transmission spectrum of the detection filter, in the wavelength range from 350 nm to 1000 nm, has
      a first stopband ($^{D}S1$) from 350 nm to $^{D}\lambda1$ with a mean transmittance of $^{D}TS1$,
      a first passband ($^{D}D1$) from $^{D}\lambda1$ to $^{D}\lambda2$ with a mean transmittance of $^{D}TD1$,
      a second stopband ($^{D}S2$) from $^{D}\lambda2$ to $^{D}\lambda3$ with a mean transmittance of $^{D}TS2$,
      a second passband ($^{D}D2$) from $^{D}\lambda3$ to $^{D}\lambda4$ with a mean transmittance of $^{D}TD2$, and
      a third stopband ($^{D}S3$) from $^{D}\lambda4$ to $^{D}\lambda5$ with a mean transmittance of $^{D}TS3$;
   wherein 350 nm$\leq^{D}\lambda1<^{D}\lambda2<^{D}\lambda3<^{D}\lambda4<^{D}\lambda5\leq1000$ nm;
   wherein $^{D}TS1<^{D}TD1$; $^{D}TD1>^{D}TS2$; $^{D}TS2<^{D}TD2$; $^{D}TD2>^{D}TS3$; and
   wherein 380 nm$\leq^{B}\lambda1\leq400$ nm; 410 nm$\leq^{B}\lambda2\leq420$ nm; 425 nm$\leq^{B}\lambda3\leq435$ nm; 465 nm$\leq^{B}\lambda4\leq485$ nm; and 850 nm$\leq^{B}\lambda5\leq1000$ nm.

2. The filter system as claimed in claim 1, wherein:
   425 nm$\leq^{D}\lambda1\leq435$ nm; 465 nm$\leq^{D}\lambda2\leq485$ nm;
   580 nm$\leq^{D}\lambda3\leq620$ nm; 650 nm$\leq^{D}\lambda4\leq770$ nm; and
   850 nm$\leq^{D}\lambda5\leq1000$ nm.

3. The filter system as claimed in claim 1, further comprising:
   the first stopband ($^{D}S1$) of the detection filter at least partly including the first passband ($^{B}D1$) of the illumination filter;
   the first passband ($^{D}D1$) of the detection filter at least partly including the second passband ($^{B}D2$) of the illumination filter; or
   the first stopband ($^{D}S1$) of the detection filter at least partly including the first passband ($^{B}D1$) of the illumination filter and the first passband ($^{P}$D1) of the detection filter at least partly including the second passband ($^{B}$D2) of the illumination filter.

4. The filter system as claimed in claim 1, wherein:
$^{B}$TS1<0.01;
$^{B}$TD1>0.5;
$^{B}$TS2<0.1;
$^{B}$TD2>0.1; and
$^{B}$TS3<0.01.

5. The filter system as claimed in claim 4, further comprising:
the third stopband ($^{B}$S3) of the illumination filter having a mean transmittance of at most 0.001 in a range from 600 nm to 750 nm.

6. The filter system as claimed in claim 1, wherein:
$^{D}$TS1<0.01;
$^{D}$TD1>0.5;
$^{D}$TS2<0.1;
$^{D}$TD2>0.5; and
$^{D}$TS3<0.01.

7. The filter system as claimed in claim 1, wherein the mean transmittance of at least one of the passbands ($^{P}$D1, $^{P}$D2) is at least 5 times greater than the mean transmittances of the stopbands ($^{P}$S1, $^{P}$S2, $^{P}$S3) spectrally adjoining the at least one of the passbands.

8. A fluorescence observation system, comprising:
a light production system, which is configured to produce excitation light for exciting fluorescence and illumination light that differs from the excitation light, and to direct the excitation light and the illumination light onto an object region;
a spatially resolving camera for detecting an image of the object region; and
an optical filter system as claimed in claim 1;
wherein the illumination filter of the filter system is arranged in a beam path between the light production system and the object region; and
wherein the detection filter of the filter system is arranged in a beam path between the object region and the camera.

9. The fluorescence observation system as claimed in claim 8, wherein the light production system comprises:
a plurality of light sources, wherein an intensity of light produced by each of the light sources is independently adjustable.

10. The fluorescence observation system as claimed in claim 8, wherein the light sources for producing excitation light emit substantially exclusively within the stopbands of the detection filter.

11. The fluorescence observation system as claimed in claim 8, the light production system for producing excitation light comprising at least one of:
a laser with a central emission wavelength of $\Lambda1$ or a narrowband violet LED with a central emission wavelength of $\Lambda2$,
wherein:

405 nm$-\Delta\Lambda_{Laser}\leq\Lambda1\leq$405 nm$+\Delta\Lambda_{Laser}$, with $\Delta\Lambda_{Laser}$=5 nm;

410 nm$-\Delta\Lambda_{LED}\leq\Lambda2\leq$410 nm$+\Delta\Lambda_{LED}$, with $\Delta\Lambda_{LED}$=20 nm; and/or a laser with a central emission wavelength of $\Lambda3$ or a narrowband cyan LED with a central emission wavelength of $\Lambda4$,
wherein:

488 nm$-\Delta\Lambda_{Laser}\leq\Lambda3\leq$488 nm$+\Delta\Lambda_{Laser}$, with $\Delta\Lambda_{Laser}$=5 nm;

490 nm$-\Delta\Lambda_{LED}\leq\Lambda4\leq$490 nm$+\Delta\Lambda_{LED}$, with $\Delta\Lambda_{LED}$=20 nm; or a laser with a central emission wavelength of $\Lambda5$ or a narrowband IR LED with a central emission wavelength of $\Lambda6$,
wherein:

785 nm$-\Delta\Lambda_{Laser}\leq\Lambda5\leq$785 nm$+\Delta\Lambda_{Laser}$, with $\Delta\Lambda_{Laser}$=5 nm;

800 nm$-\Delta\Lambda_{LED}\leq\Lambda6\leq$800 nm$+\Delta\Lambda_{LED}$, with $\Delta\Lambda_{LED}$=20 nm.

12. The fluorescence observation system as claimed in claim 8, wherein the light production system for producing illumination light comprises at least one of:
a narrowband blue LED with a central emission wavelength in the range from 450 nm$-\Delta\Lambda_{LED}$ to 450 nm$+\Delta\Lambda_{LED}$; with $\Delta\Lambda_{LED}$=20 nm;
a broadband LED, which emits light in the spectral range from 400 nm to 700 nm; or
a narrowband red LED with a central emission wavelength in the range from 660 nm$-\Delta\Lambda_{LED}$ to 660 nm$+\Delta\Lambda_{LED}$; with $\Delta\Lambda_{LED}$=20 nm.

13. The fluorescence observation system as claimed in claim 8,
wherein the camera is configured to record a first image of the object region while the excitation light and the illumination light are directed onto the object region.

14. The fluorescence observation system as claimed in claim 13,
wherein the camera is configured to record a second image of the object region while only the excitation light or only the illumination light is directed onto the object region.

15. The fluorescence observation system as claimed in claim 14, further comprising:
a fifth mode of operation,
wherein, in the fifth mode of operation of the fluorescence observation system, a laser with a central emission wavelength of $\Lambda1$, 405 nm$-\Delta\Lambda_{Laser}\leq\Lambda1\leq$405 nm$+\Delta\Lambda_{Laser}$, $\Delta\Lambda_{Laser}$=5 nm, or a narrowband violet LED with a central emission wavelength of $\Lambda2$, 410 nm$-\Delta\Lambda_{LED}\leq\Lambda2\leq$410 nm$+\Delta\Lambda_{LED}$, $\Delta\Lambda_{LED}$=20 nm, produces the excitation light, and, additionally or alternatively, a laser with a central emission wavelength of $\Lambda3$, 488 nm$-\Delta\Lambda_{Laser}\leq\Lambda3\leq$488 nm$+\Delta\Lambda_{Laser}$, $\Delta\Lambda_{Laser}$=5 nm, or a narrowband cyan LED with a central emission wavelength of $\Lambda4$, 490 nm$-\Delta\Lambda_{LED}\leq\Lambda4\leq$490 nm$+\Delta\Lambda_{LED}$, $\Delta\Lambda_{LED}$=20 nm, produces the excitation light, and
a broadband LED which emits light in the spectral range from 400 nm to 700 nm produces the illumination light.

16. The fluorescence observation system as claimed in claim 13, further comprising:
at least one of a first mode of operation, a second mode of operation, and a third mode of operation;
wherein, in the first mode of operation of the fluorescence observation system, a laser with a central emission wavelength of $\Lambda1$, 405 nm$-\Delta\Lambda_{Laser}\leq\Lambda1\leq$405 nm$+\Delta\Lambda_{Laser}$, $\Delta\Lambda_{Laser}$=5 nm, or a narrowband violet LED with a central emission wavelength of $\Lambda2$, 410 nm$-\Delta\Lambda_{LED}\leq\Lambda2\leq$410 nm$+\Delta\Lambda_{LED}$, $\Delta\Lambda_{LED}$=20 nm, produces the excitation light, and a narrowband blue LED with a central emission wavelength in the range from 450 nm−ΔΛ$_{LED}$ to 450 nm+ΔΛ$_{LED}$, ΔΛ$_{LED}$=20 nm, produces the illumination light;
  wherein, in the second mode of operation of the fluorescence observation system, a laser with a central emission wavelength Λ3, 488 nm−ΔΛ$_{Laser}$≤Λ3≤488 nm+ΔΛ$_{Laser}$, ΔΛ$_{Laser}$=5 nm, or a narrowband cyan LED with a central emission wavelength Λ4, 490 nm−ΔΛ$_{LED}$≤Λ4≤490 nm+ΔΛ$_{LED}$, ΔΛ$_{LED}$=20 nm produces the excitation light, and the narrowband blue LED with a central emission wavelength in the range from 450 nm−ΔΛ$_{LED}$ to 450 nm+ΔΛ$_{LED}$, ΔΛ$_{LED}$=20 nm, produces the illumination light; or
  wherein, in the third mode of operation of the fluorescence observation system, a laser with a central emission wavelength Λ5, 785 nm−ΔΛ$_{Laser}$≤Λ5≤785 nm+ΔΛ$_{Laser}$, ΔΛ$_{Laser}$=5 nm, or a narrowband IR LED with a central emission wavelength Λ6, 800 nm−ΔΛ$_{LED}$≤Λ6≤800 nm+ΔΛ$_{LED}$, ΔΛ$_{LED}$=20 nm, produces the excitation light, and
  a broadband LED which emits light in the spectral range from 400 nm to 700 nm produces the illumination light.

17. The fluorescence observation system as claimed in claim 16, further comprising:
  a fourth mode of operation, wherein the first mode of operation and the second mode of operation are carried out simultaneously.

18. The fluorescence observation system as claimed in claim 8,
  wherein the camera is configured to record a first image of the object region while only the excitation light is directed onto the object region and to record a second image of the object region while only the illumination light is directed onto the object region.

19. An optical filter system for observing fluorescence, comprising:
  an illumination filter; and
  a detection filter;
    wherein a transmission spectrum of the illumination filter, in a wavelength range from 350 nm to 1000 nm, has
      a first stopband ($^B$S1) from 350 nm to $^B$λ1 with a mean transmittance of $^B$TS1,
      a first passband ($^B$D1) from $^B$λ1 to $^B$λ2 with a mean transmittance of $^B$TD1,
      a second stopband ($^B$S2) from $^B$λ2 to $^B$λ3 with a mean transmittance of $^B$TS2,
      a second passband ($^B$D2) from $^B$λ3 to $^B$λ4 with a mean transmittance of $^B$TD2, and
      a third stopband ($^B$S3) from $^B$λ4 to $^{BAS}$ with a mean transmittance of $^B$TS3;
    wherein 350 nm≤$^B$λ1<$^B$λ2<$^B$λ3<$^B$λ4<$^B$λ5≤1000 nm;
    wherein $^B$TS1<$^B$TD1; $^B$TD1>$^B$TS2; $^B$TS2<$^B$TD2; $^B$TD2>$^B$TS3;
    wherein a transmission spectrum of the detection filter, in the wavelength range from 350 nm to 1000 nm, has
      a first stopband ($^P$S1) from 350 nm to $^P$λ1 with a mean transmittance of $^P$TS1,
      a first passband ($^P$D1) from $^P$λ1 to $^P$λ2 with a mean transmittance of $^P$TD1,
      a second stopband ($^P$S2) from $^P$λ2 to $^P$λ3 with a mean transmittance of $^P$TS2, a second passband ($^P$D2) from $^P$λ3 to $^P$λ4 with a mean transmittance of $^P$TD2, and
      a third stopband ($^P$S3) from $^P$λ4 to $^P$λ5 with a mean transmittance of $^P$TS3;
    wherein 350 nm≤$^P$λ1<$^P$λ2<$^P$λ3<$^P$λ4<$^P$λ5≤1000 nm;
    wherein $^P$TS1<$^P$TD1; $^P$TD1>$^P$TS2; $^P$TS2<$^P$TD2; $^P$TD2>$^P$TS3; and
    wherein 420 nm≤$^B$λ1≤440 nm; 480 nm≤$^B$λ2≤520 nm; 600 nm≤$^B$λ3≤640 nm; 680 nm≤$^B$λ4≤720 nm; 850 nm≤$^B$λ5≤1000 nm, and $^B$TD2>0.1.

20. The filter system as claimed in claim 19, wherein:
475 nm≤$^P$λ1≤495 nm; 500 nm≤$^P$λ2≤505 nm; 505 nm≤$^P$λ3≤515 nm; 680 nm≤$^P$λ4≤720 nm; and 850 nm≤$^P$λ5≤1000 nm.

21. The filter system as claimed in claim 19, wherein:
$^B$TS1<0.1;
$^B$TD1>0.5;
$^B$TS2<0.01;
$^B$TD2>0.01; and
$^B$TS3<0.01.

22. The filter system as claimed in claim 19, wherein:
$^P$TS1<0.001;
0.1>$^P$TD1>0.001;
$^B$TS2<0.001;
$^P$TD2>0.1; and
$^P$TS3<0.01.

23. An optical filter system for observing fluorescence, comprising:
  an illumination filter; and
  a detection filter;
    wherein a transmission spectrum of the illumination filter, in a wavelength range from 350 nm to 1000 nm, has
      a first stopband ($^B$S1) from 350 nm to $^B$λ1 with a mean transmittance of $^B$TS1,
      a first passband ($^B$D1) from $^B$λ1 to $^B$λ2 with a mean transmittance of $^B$TD1,
      a second stopband ($^B$S2) from $^B$λ2 to $^B$λ3 with a mean transmittance of $^B$TS2,
      a second passband ($^B$D2) from $^B$λ3 to $^B$λ4 with a mean transmittance of $^B$TD2, and
      a third stopband ($^B$S3) from $^B$λ4 to $^{BAS}$ with a mean transmittance of $^B$TS3;
    wherein 350 nm≤$^B$λ1<$^B$λ2<$^B$λ3<$^B$λ4<$^B$λ5≤1000 nm;
    wherein $^B$TS1<$^B$TD1; $^B$TD1>$^B$TS2; $^B$TS2<$^B$TD2; $^B$TD2>$^B$TS3;
    wherein a transmission spectrum of the detection filter, in the wavelength range from 350 nm to 1000 nm, has
      a first stopband ($^P$S1) from 350 nm to $^P$λ1 with a mean transmittance of $^P$TS1,
      a first passband ($^P$D1) from $^P$λ1 to $^P$λ2 with a mean transmittance of $^P$TD1,
      a second stopband ($^P$S2) from $^P$λ2 to $^P$λ3 with a mean transmittance of $^P$TS2,
      a second passband ($^P$D2) from $^P$λ3 to $^P$λ4 with a mean transmittance of $^P$TD2, and
      a third stopband ($^P$S3) from $^P$λ4 to $^P$λ5 with a mean transmittance of $^P$TS3;
    wherein 350 nm≤$^P$λ1<$^P$λ2<$^P$λ3<$^P$λ4<$^P$λ5≤1000 nm;
    wherein $^P$TS1<$^P$TD1; $^P$TD1>$^P$TS2; $^P$TS2<$^P$TD2; $^P$TD2>$^P$TS3; and
    wherein 380 nm≤$^8$λ1≤400 nm; 410 nm≤$^B$λ2≤420 nm; 440 nm≤$^B$λ3≤460 nm; 490 nm≤$^B$λ4≤505 nm; and 850 nm≤$^B$λ5≤1000 nm.

24. The filter system as claimed in claim 23, wherein:
440 nm≤$^P$λ1≤460 nm; 490 nm≤$^P$λ2≤500 nm; 505 nm≤$^P$λ3≤515 nm; 650 nm≤$^P$λ4≤770 nm; and 850 nm≤$^P$λ5≤1000 nm.

25. The filter system as claimed in claim 23, further comprising:
the second passband ($^BD2$) of the illumination filter having a mean transmittance of at least $^BW1$ within a range from $^B\lambda3$ to $^B\lambda3'$, and
the second passband ($^BD2$) of the illumination filter having a mean transmittance of at least $^BW2$ within a range from $^B\lambda3'$ to $^B\lambda4$,
wherein $^B\lambda3 < ^B\lambda3' < ^B\lambda4$ and $^BW2 > ^BW1$.

26. The filter system as claimed in claim 25, further comprising:
the range from $^D\lambda1$ to $^D\lambda1'$ within the first passband ($^DD1$) of the detection filter including the range from $^B\lambda3$ to $^B\lambda3'$ within the second passband ($^BD2$) of the illumination filter.

27. The filter system as claimed in claim 23, further comprising:
the first passband ($^DD1$) of the detection filter having a mean transmittance of at least $^DW1$ within a range from $^D\lambda1$ to $^D\lambda1'$, and
the first passband ($^DD1$) of the detection filter having a mean transmittance of at least $^DW2$ within a range from $^D\lambda1'$ to $^D\lambda2$,
wherein $^D\lambda1 < ^D\lambda1' < ^D\lambda2$ and $^DW2 < ^DW1$,
wherein 470 nm $\leq ^D\lambda1' \leq$ 490 nm, and
wherein $^DW2$ is at most 0.05.

28. The filter system as claimed in claim 23, further comprising:
the second passband ($^DD2$) of the detection filter having a mean transmittance of $^DW3$ within a range from $^D\lambda3$ to $^D\lambda3'$, and
the second passband ($^DD2$) of the detection filter having a mean transmittance of $^DW4$ within a range from $^D\lambda3'$ to $^D\lambda4$,
wherein $^DW4$ differs from $^DW3$, and
wherein $^D\lambda3 < ^D\lambda3' < ^D\lambda4$.

29. The filter system as claimed in claim 23, wherein:
$^BTS1 < 0.01$;
$^BTD1 > 0.5$;
$^BTS2 < 0.1$;
$^BTD2 > 0.5$; and
$^BTS3 < 0.01$.

30. The filter system as claimed in claim 23, wherein:
$^DTS1 < 0.01$;
$^DTD1 > 0.1$;
$^DTS2 < 0.1$;
$^DTD2 > 0.5$; and
$^DTS3 < 0.01$.

31. An optical filter system for observing fluorescence, comprising:
an illumination filter; and
a detection filter;
wherein a transmission spectrum of the illumination filter, in a wavelength range from 350 nm to 1000 nm, has
a first stopband ($^BS1$) from 350 nm to $^B\lambda1$ with a mean transmittance of $^BTS1$,
a first passband ($^BD1$) from $^B\lambda1$ to $^B\lambda2$ with a mean transmittance of $^BTD1$,
a second stopband ($^BS2$) from $^B\lambda2$ to $^B\lambda3$ with a mean transmittance of $^BTS2$,
a second passband ($^BD2$) from $^B\lambda3$ to $^B\lambda4$ with a mean transmittance of $^BTD2$, and
a third stopband ($^BS3$) from $^B\lambda4$ to $^{BAS}$ with a mean transmittance of $^BTS3$;
wherein 350 nm $\leq ^B\lambda1 < ^B\lambda2 < ^B\lambda3 < ^B\lambda4 < ^B\lambda5 \leq$ 1000 nm;
wherein $^BTS1 < ^BTD1$; $^BTD1 > ^BTS2$; $^BTS2 < ^BTD2$; $^BTD2 > ^BTS3$;
wherein a transmission spectrum of the detection filter, in the wavelength range from 350 nm to 1000 nm, has
a first stopband ($^DS1$) from 350 nm to $^D\lambda1$ with a mean transmittance of $^DTS1$,
a first passband ($^DD1$) from $^D\lambda1$ to $^D\lambda2$ with a mean transmittance of $^DTD1$,
a second stopband ($^DS2$) from $^D\lambda2$ to $^D\lambda3$ with a mean transmittance of $^DTS2$,
a second passband ($^DD2$) from $^D\lambda3$ to $^D\lambda4$ with a mean transmittance of $^DTD2$, and
a third stopband ($^DS3$) from $^D\lambda4$ to $^D\lambda5$ with a mean transmittance of $^DTS3$;
wherein 350 nm $\leq ^D\lambda1 < ^D\lambda2 < ^D\lambda3 < ^D\lambda4 < ^D\lambda5 \leq$ 1000 nm;
wherein $^DTS1 < ^DTD1$; $^DTD1 > ^DTS2$; $^DTS2 < ^DTD2$; $^DTD2 > ^DTS3$; and
wherein 380 nm $\leq ^B\lambda1 \leq$ 420 nm; 680 nm $\leq ^B\lambda2 \leq$ 720 nm; 750 nm $\leq ^B\lambda3 \leq$ 790 nm; 810 nm $\leq ^B\lambda4 \leq$ 815 nm; and 950 nm $\leq ^B\lambda5 \leq$ 1000 nm.

32. The filter system as claimed in claim 31, wherein:
380 nm $\leq ^D\lambda1 \leq$ 420 nm; 680 nm $\leq ^D\lambda2 \leq$ 720 nm;
$^B\lambda4 \leq ^D\lambda3 \leq ^B\lambda4+10$ nm; 900 nm $\leq ^D\lambda4 \leq$ 940 nm; and
940 nm $\leq ^B\lambda5 \leq$ 1000 nm.

33. The filter system as claimed in claim 31, further comprising:
the first passband of the detection filter including the first passband of the illumination filter.

34. The filter system as claimed in claim 31, further comprising:
the second stopband ($^DS2$) of the detection filter having a mean transmittance of at most 0.01 within a range from $^D\lambda2'$ to $^D\lambda3$,
wherein 760 nm $\leq ^D\lambda2' \leq$ 780 nm.

35. The filter system as claimed in claim 31, wherein:
$^BTS1 < 0.1$;
$^BTD1 > 0.5$;
$^BTS2 < 0.1$;
$^BTD2 > 0.5$; and
$^BTS3 < 0.1$.

36. The filter system as claimed in claim 31, wherein:
$^DTS1 < 0.01$;
$^DTD1 > 0.5$;
$^DTS2 < 0.1$;
$^DTD2 > 0.5$; and
$^DTS3 < 0.1$.

37. An optical filter system for observing fluorescence, comprising:
an illumination filter; and
a detection filter;
wherein a transmission spectrum of the illumination filter, in a wavelength range from 350 nm to 1000 nm, has
a first stopband ($^BS1$) from 350 nm to $^B\lambda1$ with a mean transmittance of $^BTS1$,
a first passband ($^BD1$) from $^B\lambda1$ to $^B\lambda2$ with a mean transmittance of $^BTD1$,
a second stopband ($^BS2$) from $^B\lambda2$ to $^B\lambda3$ with a mean transmittance of $^BTS2$,
a second passband ($^BD2$) from $^B\lambda3$ to $^B\lambda4$ with a mean transmittance of $^BTD2$, and
a third stopband ($^BS3$) from $^B\lambda4$ to $^{BAS}$ with a mean transmittance of $^BTS3$;
wherein 350 nm $\leq ^B\lambda1 < ^B\lambda2 < ^B\lambda3 < ^B\lambda4 < ^B\lambda5 \leq$ 1000 nm;
wherein $^BTS1 < ^BTD1$; $^BTD1 > ^BTS2$; $^BTS2 < ^BTD2$; $^BTD2 > ^BTS3$;

wherein a transmission spectrum of the detection filter, in the wavelength range from 350 nm to 1000 nm, has
    a first stopband ($^PS1$) from 350 nm to $^P\lambda1$ with a mean transmittance of $^PTS1$,
    a first passband ($^PD1$) from $^P\lambda1$ to $^P\lambda2$ with a mean transmittance of $^PTD1$, and
    a second stopband ($^PS2$) from $^P\lambda2$ to $^P\lambda3$ with a mean transmittance of $^PTS2$,
wherein 350 nm≤$^P\lambda1$<$^P\lambda2$<$^P\lambda3$≤1000 nm;
wherein $^PTS1$<$^PTD1$; $^PTD1$>$^PTS2$; and
wherein 380 nm≤$^B\lambda1$≤400 nm; 410 nm≤$^B\lambda2$≤420 nm; 440 nm≤$^B\lambda3$≤460 nm; 600 nm≤$^B\lambda4$≤800 nm; and 950 nm≤$^B\lambda5$≤1000 nm.

38. The filter system as claimed in claim 37, wherein: $^B\lambda3-5$ nm≤$^P\lambda1$≤$^B\lambda3+5$ nm; 600 nm≤$^P\lambda2$≤800 nm,
    wherein, the first passband ($^PD1$) of the detection filter includes the second passband ($^BD2$) of the illumination filter, or
    wherein $^P\lambda2$≤720 nm or $^P\lambda2$≤680 nm.

39. The filter system as claimed in claim 37, further comprising:
    the first passband ($^PD1$) of the detection filter having a mean transmittance of at least $^PW1$ within a first range from $^P\lambda1$ to $^P\lambda1'$, and
    the first passband ($^PD1$) of the detection filter has a mean transmittance of at least $^PW2$ within a second range from $^P\lambda1'$ to $^P\lambda2$,
    wherein $^PW2$>$^PW1$.

40. The filter system as claimed in claim 37, wherein:
$^BTS1$<0.01;
$^BTD1$>0.5;
$^BTS2$<0.1;
$^BTD2$>0.5; and
$^BTS3$<0.01.

41. The filter system as claimed in claim 37, wherein:
$^PTS1$<0.01;
$^PTD1$>0.5; and
$^PTS2$<0.01.

42. An optical detection filter for detecting visible light and fluorescence light, the optical detection filter comprising:
    a transmission spectrum which, between 350 nm and 1000 nm, has
        a first stopband ($^PS1$) from $^P\lambda1$ to $^P\lambda2$,
        a first passband ($^PD1$) from $^P\lambda2$ to $^P\lambda3$,
        a second stopband ($^PS2$) from $^P\lambda3$ to $^P\lambda4$,
        a second passband ($^PD2$) from $^P\lambda4$ to $^P\lambda5$,
        a third stopband ($^PS3$) from $^P\lambda5$ to $^P\lambda6$, and
        a third passband ($^PD3$) from $^P\lambda6$ to $^P\lambda7$;
    wherein the stopbands ($^PS1, ^PS2, ^PS3$) each have a mean transmittance of at most 0.01, and
    wherein the passbands ($^PD1, ^PD2$) each have a mean transmittance of at least 0.5, and
    wherein 350 nm≤$^P\lambda1$<$^P\lambda2$<$^P\lambda3$<$^P\lambda4$<$^P\lambda5$<$D\lambda6$<$^P7$<1000 nm.

43. The detection filter as claimed in claim 42, wherein:
350 nm≤$^P\lambda1$≤400 nm; 410 nm≤$^P\lambda2$≤435 nm;
465 nm≤$^P\lambda3$≤475 nm; 495 nm≤$^P\lambda4$≤515 nm;
765 nm≤$^P\lambda5$≤775 nm; 795 nm≤$^P\lambda6$≤825 nm; and
910 nm≤$^P\lambda7$≤930 nm.

44. The detection filter as claimed in claim 42, wherein the transmission spectrum further comprises:
    a fourth stopband ($^PS4$) from $^P\lambda7$ to 1000 nm.

45. The detection filter as claimed in claim 42, further comprising:
    the second passband ($^PD2$), within a spectral range from 510 nm to 750 nm, having the mean transmittance of at least 0.9.

46. The detection filter as claimed in claim 42, further comprising:
    at least one of:
        the first stopband ($^PS1$) including the spectral range from 400 nm to 410 nm;
        the second stopband ($^PS2$) including the spectral range from 475 nm to 495 nm; or
        the third stopband ($^PS3$) including the spectral range from 775 nm to 795 nm.

47. The detection filter as claimed in claim 42, wherein:
    the mean transmittance of at least one of the passbands ($^PD1, ^PD2$) is at least 5 times greater than the mean transmittances of the stopbands ($^PS1, ^PS2, ^PS3$) spectrally adjoining the at least one of the passbands ($^PD1, ^CD2$).

48. A fluorescence observation system, comprising a light production system, which is configured to produce excitation light for exciting fluorescence and illumination light that differs from the excitation light, and to direct the excitation light and the illumination light onto an object region;
    a spatially resolving camera for detecting an image of the object region; and
    a detection filter as claimed in claim 42;
    wherein the detection filter is arranged in a beam path between the object region and the camera.

\* \* \* \* \*

UNITED STATES PATENT AND TRADEMARK OFFICE
CERTIFICATE OF CORRECTION

PATENT NO. : 10,145,738 B2
APPLICATION NO. : 15/905052
DATED : December 4, 2018
INVENTOR(S) : Christoph Nieten et al.

Page 1 of 1

It is certified that error appears in the above-identified patent and that said Letters Patent is hereby corrected as shown below:

In the Specification

Column 6, Line 10: replace "$^{C}D2$" with -- $^{D}D2$ --

Column 6, Line 12: replace "$^{L}D1$" with -- $^{D}D1$ --

Column 9, Line 20: replace "$^{L}D1$" with -- $^{D}D1$ --

Column 15, Line 37: replace "BS1" with -- $^{B}S1$ --

Column 16, Line 63: replace "$^{D}S2$" with -- $^{B}S2$ --

Column 17, Line 12: replace "$^{B}D2$" with -- $^{D}D2$ --

Column 17, Line 15: replace "$^{B}D2$" with -- $^{D}D2$ --

Column 20, Line 39: replace "$^{L}D1$" with -- $^{D}D1$ --

Column 20, Line 51: replace "$^{C}D2$" with -- $^{D}D2$ --

Column 23, Line 57: replace "$^{L}D1$" with -- $^{D}D1$ --

Column 25, Line 7: replace "$^{L}D1$" with -- $^{D}D1$ --

Column 25, Line 7: replace "$^{C}D2$" with -- $^{D}D2$ --

In the Claims

Claim 47: replace "$^{C}D2$" with -- $^{D}D2$ --

Signed and Sealed this
Twenty-ninth Day of January, 2019

Andrei Iancu
*Director of the United States Patent and Trademark Office*